United States Patent
Datar et al.

(10) Patent No.: US 11,746,128 B2
(45) Date of Patent: Sep. 5, 2023

(54) COMPOSITIONS AND METHODS FOR INCREASING THE IMMUNOGLOBULIN BINDING CAPACITIES OF IMMUNOGLOBULIN-BINDING POLYPEPTIDES AND OLIGOPEPTIDES

(71) Applicant: HurraH S.A.R.L, Kehlen (LU)

(72) Inventors: Rajiv Datar, Irvine, CA (US); Carole Laine, Attert (BE); Kajal Arora, Manesar (IN)

(73) Assignee: HurraH S.A.R.L, Kehlen (LU)

( * ) Notice: Subject to any disclaimer, the term of this patent is extended or adjusted under 35 U.S.C. 154(b) by 1091 days.

(21) Appl. No.: 16/438,888

(22) Filed: Jun. 12, 2019

(65) Prior Publication Data

US 2019/0309027 A1    Oct. 10, 2019

Related U.S. Application Data

(63) Continuation of application No. PCT/EP2017/082282, filed on Dec. 11, 2017.

(60) Provisional application No. 62/432,807, filed on Dec. 12, 2016.

(51) Int. Cl.

| | |
|---|---|
| *B01D 15/38* | (2006.01) |
| *B01J 2/28* | (2006.01) |
| *C07K 1/22* | (2006.01) |
| *C07K 17/06* | (2006.01) |
| *C07K 17/08* | (2006.01) |
| *C07K 19/00* | (2006.01) |
| *C07K 14/31* | (2006.01) |
| *B01J 20/24* | (2006.01) |
| *B01J 20/26* | (2006.01) |
| *B01J 20/28* | (2006.01) |
| *C07K 16/00* | (2006.01) |

(52) U.S. Cl.
CPC .......... *C07K 14/31* (2013.01); *B01D 15/3809* (2013.01); *B01J 20/24* (2013.01); *B01J 20/261* (2013.01); *B01J 20/28092* (2013.01); *C07K 1/22* (2013.01); *C07K 16/00* (2013.01); *C07K 17/06* (2013.01); *C07K 17/08* (2013.01); *C07K 2319/705* (2013.01)

(58) Field of Classification Search
CPC ... B01D 15/3809; B01J 20/103; B01J 20/261; B01J 20/28092; B01J 20/283; B01J 20/285; B01J 20/289; C07K 1/22; C07K 16/065; C07K 17/06; C07K 17/08; C07K 17/14; C07K 2319/70; C07K 2319/705
See application file for complete search history.

(56) References Cited

U.S. PATENT DOCUMENTS

| | | | |
|---|---|---|---|
| 6,977,175 B1 * | 12/2005 | Horvitz | C07K 14/47 435/254.11 |
| 8,685,893 B2 | 4/2014 | Sidhu et al. | |
| 8,921,531 B2 * | 12/2014 | Shenoy | C07K 14/31 530/413 |
| 9,040,661 B2 | 5/2015 | Nakamura et al. | |
| 2014/0179898 A1 * | 6/2014 | Honda | C07K 14/005 536/23.7 |
| 2016/0215027 A1 * | 7/2016 | Majima | C07K 1/22 |
| 2017/0058017 A1 * | 3/2017 | Sarkar | C07K 14/775 |

FOREIGN PATENT DOCUMENTS

| | | |
|---|---|---|
| EP | 0863210 A2 | 9/1998 |
| EP | 2412809 B1 | 1/2012 |
| EP | 2532672 B2 | 6/2012 |
| EP | 2202310 B1 | 3/2013 |
| WO | WO2003080655 A1 | 2/2003 |
| WO | WO2008039141 A1 | 3/2008 |
| WO | WO2008127457 A2 | 10/2008 |
| WO | WO2012087231 A1 | 6/2012 |

OTHER PUBLICATIONS

Cao Yongsheng et al; "Charachterization of the optimized C2 domain of protein G: finding its additional chicken IgY-binding ability" Biotehcnology Letters, (2013) vol. 35, No. 9, pp. 1441-1447, XP002778983.
Ahlborg N et al; "Immunogens containing sequences from antigen PF332 induce plasmodium falciparum-reactive antibodies which inhibit parasite growth but not cytoadherence" Parasite Immunology, Blackwell Scientific Publications, Oxford, GB, vol. 17, No. 7, pp. 341-352, (1995).
Yang Hua et al; "Evolutional selection of a combinatorial phage library displaying randomly-rearranged various single domains of immunoglobulin (Ig)-binding proteins (IBPs) with four kinds of Ig molecules" BMC Micrbiology, Biomed Central Ltd, GB, vol. 8, No. 1, Aug. 13, 2008, pp. 1-13.
Gottschalk, Uwe., "Downstream processing of monoclonal antibodies: from high dilution to high purity" Jan. 6, 2005, Biopharm International, vol. 18, Issue 6: pp. 42-58.
Gülich, Susanne et al., "Engineering streptococcal protein G for increased alkaline stability" Protein Engineering, vol. 15, No. 10, 2002; pp. 835-842.
Guss, Bengt et al; "Region X, the cell-wall-attachment part of staphylococcal protein A" Departments of Microbiology and of Medical and Physiological Chemistry, The Biomedical Center, University of Uppsala; Eur. J. Biochem. 138, (1984), pp. 413-420.

(Continued)

*Primary Examiner* — Jeffrey E. Russel
(74) *Attorney, Agent, or Firm* — Vorys, Sater, Seymour, and Pease LLP

(57) ABSTRACT

Compositions and methods are provided for producing materials having increased immunoglobulin binding capacities, the materials including full-length or truncated forms of protein A, protein G, protein A/G, protein L and other immunoglobulin-binding proteins or peptides, which moieties contain polypeptide domains, or polypeptide-oligopeptide combinations. Also provided are separation matrices containing the moieties and methods of using the separation matrices for separation of immunoglobulins or immunoglobulin containing proteins.

12 Claims, 12 Drawing Sheets

Specification includes a Sequence Listing.

(56) References Cited

OTHER PUBLICATIONS

Hjelm et al., "Protein A from *Staphylococcus aureus*, its issolation by affinity chromotography and its use as an immunosorbent for isolation of immunoglobulins" FEBS Letters, vol. 28, No. 1, (1972), pp. 73-76.
Lindmark, Roger et al; "Extracellular Protein A from a Methicillin-Resistant Strain of *Staphylococcus aureus*" Eur. J. Biochem. 74, (1977), pp. 623-628.
Löfdahl, Sven et al; "Gene for staphylococcal protein A" Proc. Natl. Acad. Sci. USA, vol. 80, Feb. 1983, Biochemistry, pp. 697-701.
Sjöquist, John et al; "Protein A isolated from *Staphylococcus aureus* after digestion with lysostaphin" Eur. J. Biochem. 29, (1972), pp. 572-578.
Sjöquist, John et al; "Localization of protein A in the bacteria" Eur. J. Biochem. 30, (1972), pp. 190-194.
Bhut, Bharat V. et al; "Preparation of high-capacity, weak anion-exchange membranes for protein separations using surface-initiated atom transfer radical polymerization" Journal of Membrane Science 325 (2008), pp. 176-183.
Boschetti, Egisto; "Separation of antibodies by liquid chromatography" Jungbauer, Alois, 15, pp. 535-632, (2000).
Carter-Franklin, Jayme N.; et al., "Fragments of protein A eluted during protein A affinity chromatography" Journal of Chromatography A, 1163 (2007), pp. 105-111.
Engel, Henk; et al.; "Enzymatic preparation of 1,6-anhydro-muropeptides by immobilized murein hydrolases from *Escherichia coli* fused to staphylococcal protein A" Appl. Microbiol Biotechnol (1992) 37: pp. 772-783.
Follman, Deborah K. and Fahrner, Robert L.; "Factorial screening of antibody purification processes using three chromatography steps without, protein A" Journal of Chromatography A, 1024 (2004), pp. 79-85.
Gagnon, Pete; "Technology trends in antibody purification" Journal of Chromatography A, 1221 (2012), pp. 57-70.
Gottschalk, U., "Downstream Processing of Monoclonal Antibodies: from High Dilution to High Purity" Biopharm International; Jun. 2005; 18, 6; ProQuest Central, pp. 42-58.
Gouda, Hiroaki et al; "NMR Study of the Interaction between the B Domain of Staphylococcal Protein A and the Fc Portion of Immunoglobulin G" Biochemistry, 1998, 37, pp. 129-136.
Hahn, Rainer et al; "Hydrophobic interaction chromatography of proteins II. Binding capacity, recovery and mass transfer properties" Journal of Chromatography B, 790 (2003), pp. 99-114.
Kronvall, Göran; "A Surface Component in Group A, C, and G Streptococci With Non-Immune Reactivity for Immunoglobulin G" The Journal of Immunology, vol. 111, No. 5, Nov. 1973, pp. 1401-1406.
Kuczewski, Michael et al; "A single-use purification process for the production of a monoclonal antibody produced in a PER.C6 human ceil line" Biotechnology Journal, DOI10,1002/biot.201000292, Biotechnol. J. 2011, 6, pp. 56-65.
Langone, John J.; "Protein A of *Staphylococcus uureus* and Related Irnmunog Iobul in Receptors Produced by Streptococci and Pneumonococci" Advances in Immunology, vol. 32, pp. 157-252, (1982).
Leavy, Olive; "Therapeutic antibodies: past, present and future" Nature Reviews Immunology, vol. 10, May 2010, p. 297.
Linhult, Martin et al; "Improving the Tolerance of a Protein A Analogue to Repeated Alkaline Exposures Using a Bypass Mutagenesis Approach" Proteins: Structure, Function, and Bioinformatics 55: (2004) pp. 407-416.
Schultz, Wolfram et al; "Responses of Monkey Dopamine Neurons to Reward and Conditioned Stimuli during Succesive Steps of Learning a Delayed Response Task" The Journal of Neuroscience, Mar. 1993, 13(3): pp. 900-913.
Ljunglof, Anders et al; "Improved Capture with Better Productivity in MAb Bioprocessing" BioProcess International, Industry Yearbook 2011-2012, pp. 66-67.
Shukla, Abhinav A. et al; "Downstream processing of monoclonal antibodies—Application of platform approaches" Journal of Chromatography B, 848 (2007), pp. 28-39.
Liu, Zhihua et al; "*Drosophila* Acyl-CoA Synthetase Long-Chain Family Member 4 Regulates Axonal Transport of Synaptic Vesicles and is Required for Synaptic Development and Transmission" The Journal of Neuroscience, Feb. 9, 2011, 31 (6): pp. 2052-2063.
Saha, K.; Bender, F. and Gizeli E.; "Comparative Study of IgG Binding to Proteins G and A: Nonequilibrium Kinetic and Binding Constant Determination with the Acoustic Waveguide Device" Anal. Chem. 2003, 75, pp. 835-842.
Thillaivinayagalingam P. et al., "Biopharmaceutical Purification Strategies" 2007. Genet. Eng. Biotechn. vol. 27, No. 11, Jun. 1, 2007, pp. 1-5.
Yang H.; et al., "Hexamer peptide affinity resins that bind the Fc region of human immunoglobulin G" J. Peptide Res., 2006, 66 (Suppl. 1), pp. 120-137.
Low, Duncan; et al., "Future of antibody purification" Journal of Chromatography B, 848, (2007), pp. 48-63.
Cai, Shiying et al; "High Level Expression of Recombinant Protein A in *Escherichia coli*" Chinese Journal of Biotechnology; 8(2), 1992, pp. 123-127.
XP002778984; retrieved from EBI accession No. GSP: BCQ32089, database accession No. BCQ32089 sequence "Protein a mimetic peptide", p. 1, (2016).

\* cited by examiner

FIG. 1

Schematic map of the Staphylococcal protein A (SpA) gene.

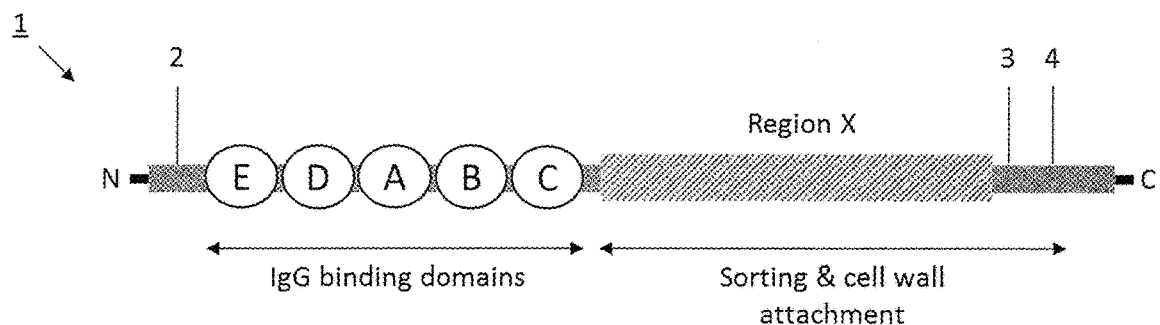

FIG. 2

Amino acid sequence of native *Staphylococcus aureus* protein A

MKKKNIYSIRKLGVGIASVTLGTLLISGGVTPAANAAQHDEAQQNAFYQVLNMPNLNAD
QRNGFIQSLKDDPSQSANVLGEAQKLNDSQAPKADAQQNNFNKDQQSAFYEILNMPNLN
EAQRNGFIQSLKDDPSQSTNVLGEAKKLNESQAPKADNNFNKEQQNAFYEILNMPNLNE
EQRNGFIQSLKDDPSQSANLLSEAKKLNESQAPKADNKFNKEQQNAFYEILHLPNLNEE
QRNGFIQSLKDDPSQSANLLAEAKKLNDAQAPKADNKFNKEQQNAFYEILHLPNLTEEQ
RNGFIQSLKDDPSVSKEILAEAKKLNDAQAPKEEDNNKPGKEDNNKPGKEDNNKPGKED
NNKPGKEDNNKPGKEDNNKPGKEDGNKPGKEDNKKPGKEDGNKPGKEDNKKPGKEDGNK
PGKEDGNKPGKEDGNGVHVVKPGDTVNDIAKANGTTADKIAADNKLADKNMIKPGQELV
VDKKQPANHADANKAQALPETGEENPFIGTTVFGGLSLALGAALLAGRRREL
(SEQ ID NO:1)

FIG. 3

Protein A amino acid sequence broken into the designated IgG binding domains

E domain
AQHDEAQQNAFYQVLNMPNLNADQRNGFIQSLKDDPSQSANVLGEAQKLNDSQAPK
(SEQ ID NO:2)

D domain
ADAQQNNFNKDQQSAFYEILNMPNLNEAQRNGFIQSLKDDPSQSTNVLGEAKKLNESQAPK
(SEQ ID NO:3)

A domain
ADNNFNKEQQNAFYEILNMPNLNEEQRNGFIQSLKDDPSQSANLLSEAKKLNESQAPK
(SEQ ID NO:4)

B domain
ADNKFNKEQQNAFYEILHLPNLNEEQRNGFIQSLKDDPSQSANLLAEAKKLNDAQAPK
(SEQ ID NO:5)

C domain
ADNKFNKEQQNAFYEILHLPNLTEEQRNGFIQSLKDDPSVSKEILAEAKKLNDAQAPK
(SEQ ID NO:6)

X domain
EEDNNKPGKEDNNKPGKEDNNKPGKEDNNKPGKEDNNKPGKEDNNKPGKEDGNKPGKED
NKKPGKEDGNKPGKEDNKKPGKEDGNKPGKEDGNKPGKEDGNGVHVVKPGDTVNDIAKA
NGTTADKIAADNKLADKNMIKPGQELVVDKKQPANHADANKAQALPETGEENPFIGTTV
FGGLSLALGAALLAGRRREL
(SEQ ID NO:7)

FIG. 4A

Schematic of an amino acid polypeptide backbone showing the repeating unit (n).

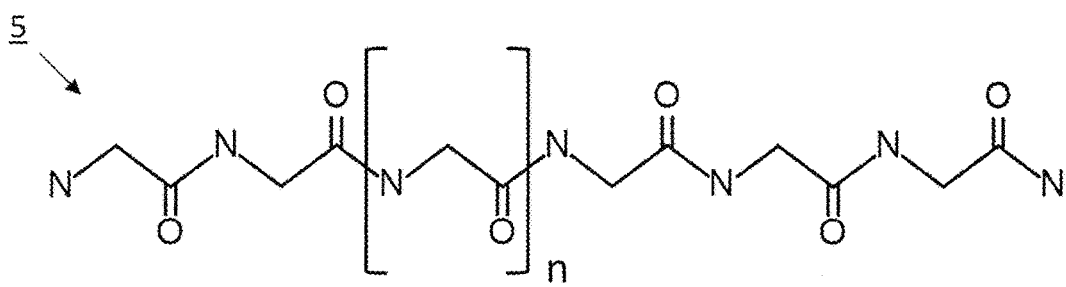

Examples of amino acid sequences with affinity for IgG binding

HWRGWV (SEQ ID NO:8)

QPQMSHM (SEQ ID NO:9)

KPGKED<u>NN</u> (SEQ ID NO:10)

Schematic of the optimum combination of binding capacity and flow rate

Schematic examples of various protein-polypeptide moiety combinations

Schematic representative of domains linked to each other and to polypeptide moieties Schematic representation of polypeptide moieties bound to a support matrix

FIG. 9

Linearity of scale up of novel bimodal porous PVC media with embedded silica particles

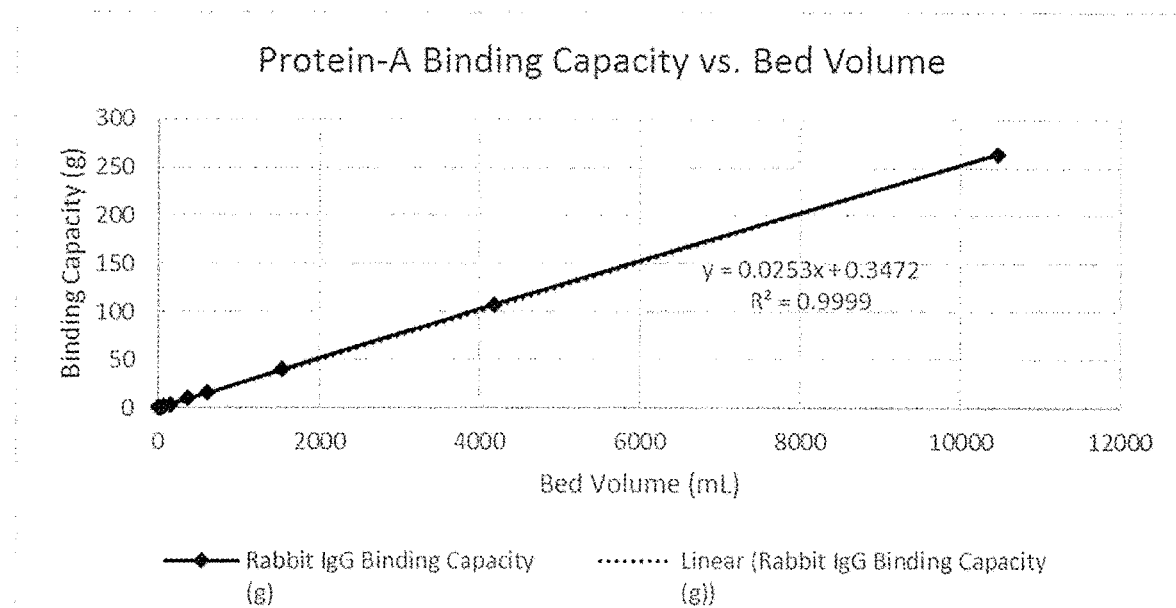

FIG. 10

SEQ ID 11: Amino Acid Sequence of Protein A for Cytosolic Expression

MAQHDEAQQNAFYQVLNMPNLNADQRNGFIQSLKDDPSQSANVLGEAQKLNDSQAPKADA
QQNNFNKDQQSAFYEILNMPNLNEAQRNGFIQSLKDDPSQSTNVLGEAKKLNESQAPKAD
NNFNKEQQNAFYEILNMPNLNEEQRNGFIQSLKDDPSQSANLLSEAKKLNESQAPKADNK
FNKEQQNAFYEILHLPNLNEEQRNGFIQSLKDDPSQSANLLAEAKKLNDAQAPKADNKFN
KEQQNAFYEILHLPNLTEEQRNGFIQSLKDDPSVSKEILAEAKKLNDAQAPKEEDNNKPG
KEDNNKPGKEDNNKPGKEDNNKPGKEDNNKPGKEDGNKPGKEDNKKPGKEDGNKPGKEDN
KKPGKEDGNKPGKEDGNKPGKEDGNGVHVVKPGDTVNDIAKANGTTADKIAADNKLADKN
MIKPGQELVVDKKQPANHADANKAQALPET

FIG. 11

SEQ ID 12: Amino Acid Sequence of Protein A for Periplasmic Expression

MKKTAIAIAVALAGFATVAQAAQHDEAQQNAFYQVLNMPNLNADQRNGFIQSLKDDPSQS
ANVLGEAQKLNDSQAPKADAQQNNFNKDQQSAFYEILNMPNLNEAQRNGFIQSLKDDPSQ
STNVLGEAKKLNESQAPKADNNFNKEQQNAFYEILNMPNLNEEQRNGFIQSLKDDPSQSA
NLLSEAKKLNESQAPKADNKFNKEQQNAFYEILHLPNLNEEQRNGFIQSLKDDPSQSANL
LAEAKKLNDAQAPKADNKFNKEQQNAFYEILHLPNLTEEQRNGFIQSLKDDPSVSKEILA
EAKKLNDAQAPKEEDNNKPGKEDNNKPGKEDNNKPGKEDNNKPGKEDNNKPGKEDGNKPG
KEDNKKPGKEDGNKPGKEDNKKPGKEDGNKPGKEDGNKPGKEDGNGVHVVKPGDTVNDIA
KANGTTADKIAADNKLADKNMIKPGQELVVDKKQPANHADANKAQALPET

FIG. 12

SEQ ID 13: Amino Acid Sequence of Protein A for Extracellular Expression

MKKKNIYSIRKLGVGIASVTLGTLLISGGVTPAANAAQHDEAQQNAFYQVLNMPNLNADQ
RNGFIQSLKDDPSQSANVLGEAQKLNDSQAPKADAQQNNFNKDQQSAFYEILNMPNLNEA
QRNGFIQSLKDDPSQSTNVLGEAKKLNESQAPKADNNFNKEQQNAFYEILNMPNLNEEQR
NGFIQSLKDDPSQSANLLSEAKKLNESQAPKADNKFNKEQQNAFYEILHLPNLNEEQRNG
FIQSLKDDPSQSANLLAEAKKLNDAQAPKADNKFNKEQQNAFYEILHLPNLTEEQRNGFI
QSLKDDPSVSKEILAEAKKLNDAQAPKEEDNNKPGKEDNNKPGKEDNNKPGKEDNNKPGK
EDNNKPGKEDGNKPGKEDNKKPGKEDGNKPGKEDNKKPGKEDGNKPGKEDGNKPGKEDGN
GVHVVKPGDTVNDIAKANGTTADKIAADNKLADKNMIKPGQELVVDKKQPANHADANKAQ
ALPET

FIG. 13

Protein A: Del

Deleted version- 415aa long

MAQHDEAQQNAFYQVLNMPNLNADQRNGFIQSLKDDPSQSANVLGEAQKLNDSQAPKADA
QQNNFNKDQQSAFYEILNMPNLNEAQRNGFIQSLKDDPSQSTNVLGEAKKLNESQAPKAD
NNFNKEQQNAFYEILNMPNLNEEQRNGFIQSLKDDPSQSANLLSEAKKLNESQAPKADNK
FNKEQQNAFYEILHLPNLNEEQRNGFIQSLKDDPSQSANLLAEAKKLNDAQAPKADNKFN
KEQQNAFYEILHLPNLTEEQRNGFIQSLKDDPSVSKEILAEAKKLNDAQAPKEEDNNKPG
KEDNNKPGKEDNNKPGKEDNNKPGKEDNNKPGKEDGNKPGKEDNKKPGKEDGNKPGKEDN
KKPGKEDGNKPGKEDGNKPGKEDGNGVHVVKPGDTVNDIAKANGTTADKIAADNK
(SEQ ID NO: 14)

Finalized sequence was with extracellular signal sequence which resulted in extracellular expression. The start codon (M) and signal sequence (boxed) get processed during expression and secretion.

450aa:

M KKKNIYSIRKLGVGIASVTLGTLLISGGVTPAANA AQHDEAQQNAFYQVLNMPNLNADQRN
GFIQSLKDDPSQSANVLGEAQKLNDSQAPKADAQQNNFNKDQQSAFYEILNMPNLNEAQRNG
FIQSLKDDPSQSTNVLGEAKKLNESQAPKADNNFNKEQQNAFYEILNMPNLNEEQRNGFIQS
LKDDPSQSANLLSEAKKLNESQAPKADNKFNKEQQNAFYEILHLPNLNEEQRNGFIQSLKDD
PSQSANLLAEAKKLNDAQAPKADNKFNKEQQNAFYEILHLPNLTEEQRNGFIQSLKDDPSVS
KEILAEAKKLNDAQAPKEEDNNKPGKEDNNKPGKEDNNKPGKEDNNKPGKEDNNKPGKEDGN
KPGKEDNKKPGKEDGNKPGKEDNKKPGKEDGNKPGKEDGNKPGKEDGNGVHVVKPGDTVNDI
AKANGTTADKIAADNK (SEQ ID NO: 15)

| Insertion point for the creation of the sequence: BIG_Hep4_lin3opt4_ExC |
|---|

| Insertion point for the creation of the sequence: BIG_Hep4_lin1opt4_ExC |
|---|

FIG. 14

BIG_Hep4_lin1opt4_ExC:

MKKKNIYSIRKLGVGIASVTLGTLLISGGVTPAANAAQHDEAQQNAFYQVLNMPNLNADQRN
GFIQSLKDDPSQSANVLGEAQKLNDSQAPKADAQQNNFNKDQQSAFYEILNMPNLNEAQRNG
FIQSLKDDPSQSTNVLGEAKKLNESQAPKADNNFNKEQQNAFYEILNMPNLNEEQRNGFIQS
LKDDPSQSANLLSEAKKLNESQAPKADNKFNKEQQNAFYEILHLPNLNEEQRNGFIQSLKDD
PSQSANLLAEAKKLNDAQAPKADNKFNKEQQNAFYEILHLPNLTEEQRNGFIQSLKDDPSVS
KEILAEAKKLNDAQAPKEEDNNGGSSRSSSSGGGGSGGGGQPQMSHMGGSSRSSSSGGGGSG
GGGQPQMSHMGGSSRSSSSGGGGSGGGGQPQMSHMGGSSRSSSSGGGGSGGGGKPGKEDNNK
PGKEDNNKPGKEDNNKPGKEDNNKPGKEDGNKPGKEDNKKPGKEDGNKPGKEDNKKPGKEDG
NKPGKEDGNKPGKEDGNGVHVVKPGDTVNDIAKANGTTADKIAADNK (SEQ ID NO: 16)

BIG_Hep4_lin3opt4_ExC:

MKKKNIYSIRKLGVGIASVTLGTLLISGGVTPAANAAQHDEAQQNAFYQVLNMPNLNADQRN
GFIQSLKDDPSQSANVLGEAQKLNDSQAPKADAQQNNFNKDQQSAFYEILNMPNLNEAQRNG
FIQSLKDDPSQSTNVLGEAKKLNESQAPKADNNFNKEQQNAFYEILNMPNLNEEQRNGFIQS
LKDDPSQSANLLSEAKKLNESQAPKADNKFNKEQQNAFYEILHLPNLNEEQRNGFIQSLKDD
PSQSANLLAEAKKLNDAQAPKADNKFNKEQQNAFYEILHLPNLTEEQRNGFIQSLKDDPSVS
KEILAEAKKLNDAQAPKGGSSRSSSSGGGGSGGGGADNKQPQMSHMHLPNLNEQPQMSHMHL
PNLNEQPQMSHMHLPNLNEVSKEILAEAKKLNDAQAPKEEDNNKPGKEDNNKPGKEDNNKPG
KEDNNKPGKEDNNKPGKEDGNKPGKEDNKKPGKEDGNKPGKEDNKKPGKEDGNKPGKEDGNK
PGKEDGNGVHVVKPGDTVNDIAKANGTTADKIAADNK (SEQ ID NO: 17)

Key:

1. The start codon encodes the first M amino acid in the above sequences.
2. The signal sequence for extracellular expression is the shaded beginning amino acid sequence in the first line of each sequence.

[ ] Sequences with different linkers/spacers containing the heptapeptide "QPQMSHM"

BIG_Hep4_lin1opt4_ExC cloned in pET30b+ expression vector

SEQUENCE LISTING

```
<160> NUMBER OF SEQ ID NOS: 23

<210> SEQ ID NO 1
<211> LENGTH: 524
<212> TYPE: PRT
<213> ORGANISM: Artificial Sequence
<220> FEATURE:
<223> OTHER INFORMATION: The sequence was designed and synthesized.

<400> SEQUENCE: 1

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
```

```
                210                 215                 220
Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
                260                 265                 270

Lys Phe Asn Lys Glu Gln Gln Asn Ala Phe Tyr Glu Ile Leu His Leu
            275                 280                 285

Pro Asn Leu Thr Glu Glu Gln Arg Asn Gly Phe Ile Gln Ser Leu Lys
            290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Lys Pro Gly Lys
                325                 330                 335

Glu Asp Asn Asn Lys Pro Gly Lys Glu Asp Asn Asn Lys Pro Gly Lys
                340                 345                 350

Glu Asp Asn Asn Lys Pro Gly Lys Glu Asp Asn Asn Lys Pro Gly Lys
                355                 360                 365

Glu Asp Asn Asn Lys Pro Gly Lys Glu Asp Gly Asn Lys Pro Gly Lys
                370                 375                 380

Glu Asp Asn Lys Lys Pro Gly Lys Glu Asp Gly Asn Lys Pro Gly Lys
385                 390                 395                 400

Glu Asp Asn Lys Lys Pro Gly Lys Glu Asp Gly Asn Lys Pro Gly Lys
                405                 410                 415

Glu Asp Gly Asn Lys Pro Gly Lys Glu Asp Gly Asn Gly Val His Val
                420                 425                 430

Val Lys Pro Gly Asp Thr Val Asn Asp Ile Ala Lys Ala Asn Gly Thr
            435                 440                 445

Thr Ala Asp Lys Ile Ala Ala Asp Asn Lys Leu Ala Asp Lys Asn Met
            450                 455                 460

Ile Lys Pro Gly Gln Glu Leu Val Val Asp Lys Lys Gln Pro Ala Asn
465                 470                 475                 480

His Ala Asp Ala Asn Lys Ala Gln Ala Leu Pro Glu Thr Gly Glu Glu
                485                 490                 495

Asn Pro Phe Ile Gly Thr Thr Val Phe Gly Gly Leu Ser Leu Ala Leu
                500                 505                 510

Gly Ala Ala Leu Leu Ala Gly Arg Arg Arg Glu Leu
            515                 520

<210> SEQ ID NO 2
<211> LENGTH: 56
<212> TYPE: PRT
<213> ORGANISM: Artificial Sequence
<220> FEATURE:
<223> OTHER INFORMATION: The sequence was designed and synthesized.

<400> SEQUENCE: 2

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
                20                  25                  30

Lys Asp Asp Pro Ser Gln Ser Ala Asn Val Leu Gly Glu Ala Gln Lys
            35                  40                  45

Leu Asn Asp Ser Gln Ala Pro Lys
            50                  55
```

```
                50                  55

<210> SEQ ID NO 3
<211> LENGTH: 61
<212> TYPE: PRT
<213> ORGANISM: Artificial Sequence
<220> FEATURE:
<223> OTHER INFORMATION: The sequence was designed and synthesized.

<400> SEQUENCE: 3

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 4
<211> LENGTH: 58
<212> TYPE: PRT
<213> ORGANISM: Artificial Sequence
<220> FEATURE:
<223> OTHER INFORMATION: The sequence was designed and synthesized.

<400> SEQUENCE: 4

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
    50                  55

<210> SEQ ID NO 5
<211> LENGTH: 58
<212> TYPE: PRT
<213> ORGANISM: Artificial Sequence
<220> FEATURE:
<223> OTHER INFORMATION: The sequence was designed and synthesized.

<400> SEQUENCE: 5

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 6
<211> LENGTH: 58
<212> TYPE: PRT
<213> ORGANISM: Artificial Sequence
<220> FEATURE:
<223> OTHER INFORMATION: The sequence was designed and synthesized.

<400> SEQUENCE: 6

Ala Asp Asn Lys Phe Asn Lys Glu Gln Gln Asn Ala Phe Tyr Glu Ile
```

```
                1               5                   10                  15
Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
        50                  55

<210> SEQ ID NO 7
<211> LENGTH: 197
<212> TYPE: PRT
<213> ORGANISM: Artificial Sequence
<220> FEATURE:
<223> OTHER INFORMATION: The sequence was designed and synthesized.

<400> SEQUENCE: 7

Glu Glu Asp Asn Asn Lys Pro Gly Lys Glu Asp Asn Asn Lys Pro Gly
1               5                   10                  15

Lys Glu Asp Asn Asn Lys Pro Gly Lys Glu Asp Asn Asn Lys Pro Gly
            20                  25                  30

Lys Glu Asp Asn Asn Lys Pro Gly Lys Glu Asp Asn Asn Lys Pro Gly
        35                  40                  45

Lys Glu Asp Gly Asn Lys Pro Gly Lys Glu Asp Asn Lys Lys Pro Gly
    50                  55                  60

Lys Glu Asp Gly Asn Lys Pro Gly Lys Glu Asp Asn Lys Lys Pro Gly
65                  70                  75                  80

Lys Glu Asp Gly Asn Lys Pro Gly Lys Glu Asp Gly Asn Lys Pro Gly
            85                  90                  95

Lys Glu Asp Gly Asn Gly Val His Val Val Lys Pro Gly Asp Thr Val
                100                 105                 110

Asn Asp Ile Ala Lys Ala Asn Gly Thr Thr Ala Asp Lys Ile Ala Ala
            115                 120                 125

Asp Asn Lys Leu Ala Asp Lys Asn Met Ile Lys Pro Gly Gln Glu Leu
        130                 135                 140

Val Val Asp Lys Lys Gln Pro Ala Asn His Ala Asp Ala Asn Lys Ala
145                 150                 155                 160

Gln Ala Leu Pro Glu Thr Gly Glu Glu Asn Pro Phe Ile Gly Thr Thr
                165                 170                 175

Val Phe Gly Gly Leu Ser Leu Ala Leu Gly Ala Ala Leu Leu Ala Gly
            180                 185                 190

Arg Arg Arg Glu Leu
        195

<210> SEQ ID NO 8
<211> LENGTH: 6
<212> TYPE: PRT
<213> ORGANISM: Artificial Sequence
<220> FEATURE:
<223> OTHER INFORMATION: The sequence was designed and synthesized.

<400> SEQUENCE: 8

His Trp Arg Gly Trp Val
1               5

<210> SEQ ID NO 9
<211> LENGTH: 7
<212> TYPE: PRT
<213> ORGANISM: Artificial Sequence
<220> FEATURE:
```

<223> OTHER INFORMATION: The sequence was designed and synthesized.

<400> SEQUENCE: 9

Gln Pro Gln Met Ser His Met
1               5

<210> SEQ ID NO 10
<211> LENGTH: 8
<212> TYPE: PRT
<213> ORGANISM: Artificial Sequence
<220> FEATURE:
<223> OTHER INFORMATION: The sequence was designed and synthesized.

<400> SEQUENCE: 10

Lys Pro Gly Lys Glu Asp Asn Asn
1               5

<210> SEQ ID NO 11
<211> LENGTH: 450
<212> TYPE: PRT
<213> ORGANISM: Staphylococcus aureus

<400> SEQUENCE: 11

Met Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
                20                  25                  30

Leu Lys Asp Asp Pro Ser Gln Ser Ala Asn Val Leu Gly Glu Ala Gln
            35                  40                  45

Lys Leu Asn Asp Ser Gln Ala Pro Lys Ala Asp Ala Gln Gln Asn Asn
        50                  55                  60

Phe Asn Lys Asp Gln Gln Ser Ala Phe Tyr Glu Ile Leu Asn Met Pro
65                  70                  75                  80

Asn Leu Asn Glu Ala Gln Arg Asn Gly Phe Ile Gln Ser Leu Lys Asp
                85                  90                  95

Asp Pro Ser Gln Ser Thr Asn Val Leu Gly Glu Ala Lys Lys Leu Asn
            100                 105                 110

Glu Ser Gln Ala Pro Lys Ala Asp Asn Asn Phe Asn Lys Glu Gln Gln
        115                 120                 125

Asn Ala Phe Tyr Glu Ile Leu Asn Met Pro Asn Leu Asn Glu Glu Gln
    130                 135                 140

Arg Asn Gly Phe Ile Gln Ser Leu Lys Asp Asp Pro Ser Gln Ser Ala
145                 150                 155                 160

Asn Leu Leu Ser Glu Ala Lys Lys Leu Asn Glu Ser Gln Ala Pro Lys
                165                 170                 175

Ala Asp Asn Lys Phe Asn Lys Glu Gln Gln Asn Ala Phe Tyr Glu Ile
            180                 185                 190

Leu His Leu Pro Asn Leu Asn Glu Glu Gln Arg Asn Gly Phe Ile Gln
        195                 200                 205

Ser Leu Lys Asp Asp Pro Ser Gln Ser Ala Asn Leu Leu Ala Glu Ala
    210                 215                 220

Lys Lys Leu Asn Asp Ala Gln Ala Pro Lys Ala Asp Asn Lys Phe Asn
225                 230                 235                 240

Lys Glu Gln Gln Asn Ala Phe Tyr Glu Ile Leu His Leu Pro Asn Leu
                245                 250                 255

Thr Glu Glu Gln Arg Asn Gly Phe Ile Gln Ser Leu Lys Asp Asp Pro
            260                 265                 270

```
Ser Val Ser Lys Glu Ile Leu Ala Glu Ala Lys Lys Leu Asn Asp Ala
            275                 280                 285

Gln Ala Pro Lys Glu Asp Asn Asn Lys Pro Gly Lys Glu Asp Asn
        290                 295                 300

Asn Lys Pro Gly Lys Glu Asp Asn Asn Lys Pro Gly Lys Glu Asp Asn
305                 310                 315                 320

Asn Lys Pro Gly Lys Glu Asp Asn Asn Lys Pro Gly Lys Glu Asp Gly
                325                 330                 335

Asn Lys Pro Gly Lys Glu Asp Asn Lys Pro Gly Lys Glu Asp Gly
            340                 345                 350

Asn Lys Pro Gly Lys Glu Asp Asn Lys Lys Pro Gly Lys Glu Asp Gly
            355                 360                 365

Asn Lys Pro Gly Lys Glu Asp Gly Asn Lys Pro Gly Lys Glu Asp Gly
            370                 375                 380

Asn Gly Val His Val Val Lys Pro Gly Asp Thr Val Asn Asp Ile Ala
385                 390                 395                 400

Lys Ala Asn Gly Thr Thr Ala Asp Lys Ile Ala Ala Asp Asn Lys Leu
                405                 410                 415

Ala Asp Lys Asn Met Ile Lys Pro Gly Gln Glu Leu Val Val Asp Lys
                420                 425                 430

Lys Gln Pro Ala Asn His Ala Asp Ala Asn Lys Ala Gln Ala Leu Pro
            435                 440                 445

Glu Thr
    450

<210> SEQ ID NO 12
<211> LENGTH: 470
<212> TYPE: PRT
<213> ORGANISM: Artificial Sequence
<220> FEATURE:
<223> OTHER INFORMATION: The sequence was designed and synthesized.

<400> SEQUENCE: 12

Met Lys Lys Thr Ala Ile Ala Ile Ala Val Ala Leu Ala Gly Phe Ala
1               5                   10                  15

Thr Val Ala Gln Ala Ala Gln His Asp Glu Ala Gln Gln Asn Ala Phe
            20                  25                  30

Tyr Gln Val Leu Asn Met Pro Asn Leu Asn Ala Asp Gln Arg Asn Gly
        35                  40                  45

Phe Ile Gln Ser Leu Lys Asp Asp Pro Ser Gln Ser Ala Asn Val Leu
50                  55                  60

Gly Glu Ala Gln Lys Leu Asn Asp Ser Gln Ala Pro Lys Ala Asp Ala
65                  70                  75                  80

Gln Gln Asn Asn Phe Asn Lys Asp Gln Gln Ser Ala Phe Tyr Glu Ile
                85                  90                  95

Leu Asn Met Pro Asn Leu Asn Glu Ala Gln Arg Asn Gly Phe Ile Gln
            100                 105                 110

Ser Leu Lys Asp Asp Pro Ser Gln Ser Thr Asn Val Leu Gly Glu Ala
        115                 120                 125

Lys Lys Leu Asn Glu Ser Gln Ala Pro Lys Ala Asp Asn Asn Phe Asn
130                 135                 140

Lys Glu Gln Gln Asn Ala Phe Tyr Glu Ile Leu Asn Met Pro Asn Leu
145                 150                 155                 160

Asn Glu Glu Gln Arg Asn Gly Phe Ile Gln Ser Leu Lys Asp Asp Pro
                165                 170                 175
```

```
Ser Gln Ser Ala Asn Leu Leu Ser Glu Ala Lys Lys Leu Asn Glu Ser
                180                 185                 190

Gln Ala Pro Lys Ala Asp Asn Lys Phe Asn Lys Glu Gln Gln Asn Ala
            195                 200                 205

Phe Tyr Glu Ile Leu His Leu Pro Asn Leu Asn Glu Glu Gln Arg Asn
        210                 215                 220

Gly Phe Ile Gln Ser Leu Lys Asp Asp Pro Ser Gln Ser Ala Asn Leu
225                 230                 235                 240

Leu Ala Glu Ala Lys Lys Leu Asn Asp Ala Gln Ala Pro Lys Ala Asp
                245                 250                 255

Asn Lys Phe Asn Lys Glu Gln Gln Asn Ala Phe Tyr Glu Ile Leu His
            260                 265                 270

Leu Pro Asn Leu Thr Glu Glu Gln Arg Asn Gly Phe Ile Gln Ser Leu
        275                 280                 285

Lys Asp Asp Pro Ser Val Ser Lys Glu Ile Leu Ala Glu Ala Lys Lys
290                 295                 300

Leu Asn Asp Ala Gln Ala Pro Lys Glu Asp Asn Asn Lys Pro Gly
305                 310                 315                 320

Lys Glu Asp Asn Asn Lys Pro Gly Lys Glu Asp Asn Asn Lys Pro Gly
                325                 330                 335

Lys Glu Asp Asn Asn Lys Pro Gly Lys Glu Asp Asn Asn Lys Pro Gly
            340                 345                 350

Lys Glu Asp Gly Asn Lys Pro Gly Lys Glu Asp Asn Lys Pro Gly
            355                 360                 365

Lys Glu Asp Gly Asn Lys Pro Gly Lys Glu Asp Asn Lys Lys Pro Gly
            370                 375                 380

Lys Glu Asp Gly Asn Lys Pro Gly Lys Glu Asp Gly Asn Lys Pro Gly
385                 390                 395                 400

Lys Glu Asp Gly Asn Gly Val His Val Val Lys Pro Gly Asp Thr Val
                405                 410                 415

Asn Asp Ile Ala Lys Ala Asn Gly Thr Thr Ala Asp Lys Ile Ala Ala
            420                 425                 430

Asp Asn Lys Leu Ala Asp Lys Asn Met Ile Lys Pro Gly Gln Glu Leu
            435                 440                 445

Val Val Asp Lys Lys Gln Pro Ala Asn His Ala Asp Ala Asn Lys Ala
        450                 455                 460

Gln Ala Leu Pro Glu Thr
465                 470

<210> SEQ ID NO 13
<211> LENGTH: 485
<212> TYPE: PRT
<213> ORGANISM: Artificial Sequence
<220> FEATURE:
<223> OTHER INFORMATION: The sequence was designed and synthesized.

<400> SEQUENCE: 13

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60
```

-continued

```
Ile Gln Ser Leu Lys Asp Asp Pro Ser Gln Ser Ala Asn Val Leu Gly
 65                  70                  75                  80

Glu Ala Gln Lys Leu Asn Asp Ser Gln Ala Pro Lys Ala Asp Ala Gln
                 85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
        275                 280                 285

Pro Asn Leu Thr Glu Glu Gln Arg Asn Gly Phe Ile Gln Ser Leu Lys
    290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Lys Pro Gly Lys
                325                 330                 335

Glu Asp Asn Asn Lys Pro Gly Lys Glu Asp Asn Asn Lys Pro Gly Lys
            340                 345                 350

Glu Asp Asn Asn Lys Pro Gly Lys Glu Asp Asn Asn Lys Pro Gly Lys
        355                 360                 365

Glu Asp Gly Asn Lys Pro Gly Lys Glu Asp Asn Lys Lys Pro Gly Lys
    370                 375                 380

Glu Asp Gly Asn Lys Pro Gly Lys Glu Asp Asn Lys Lys Pro Gly Lys
385                 390                 395                 400

Glu Asp Gly Asn Lys Pro Gly Lys Glu Asp Gly Asn Lys Pro Gly Lys
                405                 410                 415

Glu Asp Gly Asn Gly Val His Val Val Lys Pro Gly Asp Thr Val Asn
            420                 425                 430

Asp Ile Ala Lys Ala Asn Gly Thr Thr Ala Asp Lys Ile Ala Ala Asp
        435                 440                 445

Asn Lys Leu Ala Asp Lys Asn Met Ile Lys Pro Gly Gln Glu Leu Val
    450                 455                 460

Val Asp Lys Lys Gln Pro Ala Asn His Ala Asp Ala Asn Lys Ala Gln
465                 470                 475                 480

Ala Leu Pro Glu Thr
```

```
                                  485
```

<210> SEQ ID NO 14
<211> LENGTH: 415
<212> TYPE: PRT
<213> ORGANISM: Artificial Sequence
<220> FEATURE:
<223> OTHER INFORMATION: The sequence was designed and synthesized.

<400> SEQUENCE: 14

```
Met Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Gln
        35                  40                  45

Lys Leu Asn Asp Ser Gln Ala Pro Lys Ala Asp Ala Gln Gln Asn Asn
    50                  55                  60

Phe Asn Lys Asp Gln Gln Ser Ala Phe Tyr Glu Ile Leu Asn Met Pro
65                  70                  75                  80

Asn Leu Asn Glu Ala Gln Arg Asn Gly Phe Ile Gln Ser Leu Lys Asp
                85                  90                  95

Asp Pro Ser Gln Ser Thr Asn Val Leu Gly Glu Ala Lys Lys Leu Asn
            100                 105                 110

Glu Ser Gln Ala Pro Lys Ala Asp Asn Asn Phe Asn Lys Glu Gln Gln
        115                 120                 125

Asn Ala Phe Tyr Glu Ile Leu Asn Met Pro Asn Leu Asn Glu Glu Gln
    130                 135                 140

Arg Asn Gly Phe Ile Gln Ser Leu Lys Asp Asp Pro Ser Gln Ser Ala
145                 150                 155                 160

Asn Leu Leu Ser Glu Ala Lys Lys Leu Asn Glu Ser Gln Ala Pro Lys
                165                 170                 175

Ala Asp Asn Lys Phe Asn Lys Glu Gln Gln Asn Ala Phe Tyr Glu Ile
            180                 185                 190

Leu His Leu Pro Asn Leu Asn Glu Glu Gln Arg Asn Gly Phe Ile Gln
        195                 200                 205

Ser Leu Lys Asp Asp Pro Ser Gln Ser Ala Asn Leu Leu Ala Glu Ala
    210                 215                 220

Lys Lys Leu Asn Asp Ala Gln Ala Pro Lys Ala Asp Asn Lys Phe Asn
225                 230                 235                 240

Lys Glu Gln Gln Asn Ala Phe Tyr Glu Ile Leu His Leu Pro Asn Leu
                245                 250                 255

Thr Glu Glu Gln Arg Asn Gly Phe Ile Gln Ser Leu Lys Asp Asp Pro
            260                 265                 270

Ser Val Ser Lys Glu Ile Leu Ala Glu Ala Lys Lys Leu Asn Asp Ala
        275                 280                 285

Gln Ala Pro Lys Glu Glu Asp Asn Asn Lys Pro Gly Lys Glu Asp Asn
    290                 295                 300

Asn Lys Pro Gly Lys Glu Asp Asn Asn Lys Pro Gly Lys Glu Asp Asn
305                 310                 315                 320

Asn Lys Pro Gly Lys Glu Asp Asn Asn Lys Pro Gly Lys Glu Asp Gly
                325                 330                 335

Asn Lys Pro Gly Lys Glu Asp Asn Lys Lys Pro Gly Lys Glu Asp Gly
            340                 345                 350

Asn Lys Pro Gly Lys Glu Asp Asn Lys Lys Pro Gly Lys Glu Asp Gly
```

```
                355                 360                 365
Asn Lys Pro Gly Lys Glu Asp Gly Asn Lys Pro Gly Lys Glu Asp Gly
            370                 375                 380

Asn Gly Val His Val Val Lys Pro Gly Asp Thr Val Asn Asp Ile Ala
385                 390                 395                 400

Lys Ala Asn Gly Thr Thr Ala Asp Lys Ile Ala Asp Asn Lys
                405                 410                 415

<210> SEQ ID NO 15
<211> LENGTH: 450
<212> TYPE: PRT
<213> ORGANISM: Artificial Sequence
<220> FEATURE:
<223> OTHER INFORMATION: The sequence was designed and synthesized.

<400> SEQUENCE: 15

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
        275                 280                 285

Pro Asn Leu Thr Glu Glu Gln Arg Asn Gly Phe Ile Gln Ser Leu Lys
    290                 295                 300

Asp Asp Pro Ser Val Ser Lys Glu Ile Leu Ala Glu Ala Lys Lys Leu
```

```
                305                 310                 315                 320
Asn Asp Ala Gln Ala Pro Lys Glu Glu Asp Asn Asn Lys Pro Gly Lys
                325                 330                 335
Glu Asp Asn Asn Lys Pro Gly Lys Glu Asp Asn Asn Lys Pro Gly Lys
                340                 345                 350
Glu Asp Asn Asn Lys Pro Gly Lys Glu Asp Asn Asn Lys Pro Gly Lys
                355                 360                 365
Glu Asp Gly Asn Lys Pro Gly Lys Glu Asp Asn Lys Lys Pro Gly Lys
                370                 375                 380
Glu Asp Gly Asn Lys Pro Gly Lys Glu Asp Asn Lys Lys Pro Gly Lys
385                 390                 395                 400
Glu Asp Gly Asn Lys Pro Gly Lys Glu Asp Gly Asn Lys Pro Gly Lys
                405                 410                 415
Glu Asp Gly Asn Gly Val His Val Lys Pro Gly Asp Thr Val Asn
                420                 425                 430
Asp Ile Ala Lys Ala Asn Gly Thr Thr Ala Asp Lys Ile Ala Ala Asp
                435                 440                 445
Asn Lys
    450

<210> SEQ ID NO 16
<211> LENGTH: 543
<212> TYPE: PRT
<213> ORGANISM: Artificial Sequence
<220> FEATURE:
<223> OTHER INFORMATION: The sequence was designed and synthesized.

<400> SEQUENCE: 16

Met Lys Lys Lys Asn Ile Tyr Ser Ile Arg Lys Leu Gly Val Gly Ile
1               5                   10                  15
Ala Ser Val Thr Leu Gly Thr Leu Leu Ile Ser Gly Gly Val Thr Pro
                20                  25                  30
Ala Ala Asn Ala Ala Gln His Asp Glu Ala Gln Gln Asn Ala Phe Tyr
            35                  40                  45
Gln Val Leu Asn Met Pro Asn Leu Asn Ala Asp Gln Arg Asn Gly Phe
        50                  55                  60
Ile Gln Ser Leu Lys Asp Asp Pro Ser Gln Ser Ala Asn Val Leu Gly
65                  70                  75                  80
Glu Ala Gln Lys Leu Asn Asp Ser Gln Ala Pro Lys Ala Asp Ala Gln
                85                  90                  95
Gln Asn Asn Phe Asn Lys Asp Gln Gln Ser Ala Phe Tyr Glu Ile Leu
            100                 105                 110
Asn Met Pro Asn Leu Asn Glu Ala Gln Arg Asn Gly Phe Ile Gln Ser
        115                 120                 125
Leu Lys Asp Asp Pro Ser Gln Ser Thr Asn Val Leu Gly Glu Ala Lys
130                 135                 140
Lys Leu Asn Glu Ser Gln Ala Pro Lys Ala Asp Asn Asn Phe Asn Lys
145                 150                 155                 160
Glu Gln Gln Asn Ala Phe Tyr Glu Ile Leu Asn Met Pro Asn Leu Asn
                165                 170                 175
Glu Glu Gln Arg Asn Gly Phe Ile Gln Ser Leu Lys Asp Asp Pro Ser
            180                 185                 190
Gln Ser Ala Asn Leu Leu Ser Glu Ala Lys Lys Leu Asn Glu Ser Gln
        195                 200                 205
Ala Pro Lys Ala Asp Asn Lys Phe Asn Lys Glu Gln Gln Asn Ala Phe
```

```
            210                 215                 220
Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
        275                 280                 285

Pro Asn Leu Thr Glu Glu Gln Arg Asn Gly Phe Ile Gln Ser Leu Lys
    290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Gly Gly Ser Ser
                325                 330                 335

Arg Ser Ser Ser Ser Gly Gly Gly Ser Gly Gly Gly Gln Pro
                340                 345                 350

Gln Met Ser His Met Gly Gly Ser Ser Arg Ser Ser Ser Ser Gly Gly
            355                 360                 365

Gly Gly Ser Gly Gly Gly Gln Pro Gln Met Ser His Met Gly Gly
        370                 375                 380

Ser Ser Arg Ser Ser Ser Ser Gly Gly Gly Ser Gly Gly Gly Gly
385                 390                 395                 400

Gln Pro Gln Met Ser His Met Gly Gly Ser Ser Arg Ser Ser Ser Ser
                405                 410                 415

Gly Gly Gly Gly Ser Gly Gly Gly Lys Pro Gly Lys Glu Asp Asn
            420                 425                 430

Asn Lys Pro Gly Lys Glu Asp Asn Asn Lys Pro Gly Lys Glu Asp Asn
        435                 440                 445

Asn Lys Pro Gly Lys Glu Asp Asn Asn Lys Pro Gly Lys Glu Asp Gly
450                 455                 460

Asn Lys Pro Gly Lys Glu Asp Asn Lys Lys Pro Gly Lys Glu Asp Gly
465                 470                 475                 480

Asn Lys Pro Gly Lys Glu Asp Asn Lys Lys Pro Gly Lys Glu Asp Gly
                485                 490                 495

Asn Lys Pro Gly Lys Glu Asp Gly Asn Lys Pro Gly Lys Glu Asp Gly
            500                 505                 510

Asn Gly Val His Val Lys Pro Gly Asp Thr Val Asn Asp Ile Ala
        515                 520                 525

Lys Ala Asn Gly Thr Thr Ala Asp Lys Ile Ala Ala Asp Asn Lys
    530                 535                 540

<210> SEQ ID NO 17
<211> LENGTH: 533
<212> TYPE: PRT
<213> ORGANISM: Artificial Sequence
<220> FEATURE:
<223> OTHER INFORMATION: The sequence was designed and synthesized.

<400> SEQUENCE: 17

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
```

```
                35                  40                  45
Gln Val Leu Asn Met Pro Asn Leu Asn Ala Asp Gln Arg Asn Gly Phe
 50                  55                  60
Ile Gln Ser Leu Lys Asp Asp Pro Ser Gln Ser Ala Asn Val Leu Gly
 65                  70                  75                  80
Glu Ala Gln Lys Leu Asn Asp Ser Gln Ala Pro Lys Ala Asp Ala Gln
                 85                  90                  95
Gln Asn Asn Phe Asn Lys Asp Gln Gln Ser Ala Phe Tyr Glu Ile Leu
                100                 105                 110
Asn Met Pro Asn Leu Asn Glu Ala Gln Arg Asn Gly Phe Ile Gln Ser
                115                 120                 125
Leu Lys Asp Asp Pro Ser Gln Ser Thr Asn Val Leu Gly Glu Ala Lys
                130                 135                 140
Lys Leu Asn Glu Ser Gln Ala Pro Lys Ala Asp Asn Asn Phe Asn Lys
145                 150                 155                 160
Glu Gln Gln Asn Ala Phe Tyr Glu Ile Leu Asn Met Pro Asn Leu Asn
                165                 170                 175
Glu Glu Gln Arg Asn Gly Phe Ile Gln Ser Leu Lys Asp Asp Pro Ser
                180                 185                 190
Gln Ser Ala Asn Leu Leu Ser Glu Ala Lys Lys Leu Asn Glu Ser Gln
                195                 200                 205
Ala Pro Lys Ala Asp Asn Lys Phe Asn Lys Glu Gln Gln Asn Ala Phe
210                 215                 220
Tyr Glu Ile Leu His Leu Pro Asn Leu Asn Glu Glu Gln Arg Asn Gly
225                 230                 235                 240
Phe Ile Gln Ser Leu Lys Asp Asp Pro Ser Gln Ser Ala Asn Leu Leu
                245                 250                 255
Ala Glu Ala Lys Lys Leu Asn Asp Ala Gln Ala Pro Lys Ala Asp Asn
                260                 265                 270
Lys Phe Asn Lys Glu Gln Gln Asn Ala Phe Tyr Glu Ile Leu His Leu
                275                 280                 285
Pro Asn Leu Thr Glu Glu Gln Arg Asn Gly Phe Ile Gln Ser Leu Lys
                290                 295                 300
Asp Asp Pro Ser Val Ser Lys Glu Ile Leu Ala Glu Ala Lys Lys Leu
305                 310                 315                 320
Asn Asp Ala Gln Ala Pro Lys Gly Gly Ser Ser Arg Ser Ser Ser Ser
                325                 330                 335
Gly Gly Gly Gly Ser Gly Gly Gly Ala Asp Asn Lys Gln Pro Gln
                340                 345                 350
Met Ser His Met His Leu Pro Asn Leu Asn Glu Gln Pro Gln Met Ser
                355                 360                 365
His Met His Leu Pro Asn Leu Asn Glu Gln Pro Gln Met Ser His Met
                370                 375                 380
His Leu Pro Asn Leu Asn Glu Val Ser Lys Glu Ile Leu Ala Glu Ala
385                 390                 395                 400
Lys Lys Leu Asn Asp Ala Gln Ala Pro Lys Glu Glu Asp Asn Asn Lys
                405                 410                 415
Pro Gly Lys Glu Asp Asn Asn Lys Pro Gly Lys Glu Asp Asn Asn Lys
                420                 425                 430
Pro Gly Lys Glu Asp Asn Asn Lys Pro Gly Lys Glu Asp Asn Asn Lys
                435                 440                 445
Pro Gly Lys Glu Asp Gly Asn Lys Pro Gly Lys Glu Asp Asn Lys Lys
                450                 455                 460
```

```
Pro Gly Lys Glu Asp Gly Asn Lys Pro Gly Lys Glu Asp Asn Lys Lys
465                 470                 475                 480

Pro Gly Lys Glu Asp Gly Asn Lys Pro Gly Lys Glu Asp Gly Asn Lys
                    485                 490                 495

Pro Gly Lys Glu Asp Gly Asn Gly Val His Val Val Lys Pro Gly Asp
                500                 505                 510

Thr Val Asn Asp Ile Ala Lys Ala Asn Gly Thr Thr Ala Asp Lys Ile
        515                 520                 525

Ala Ala Asp Asn Lys
    530

<210> SEQ ID NO 18
<211> LENGTH: 7
<212> TYPE: PRT
<213> ORGANISM: Artificial Sequence
<220> FEATURE:
<223> OTHER INFORMATION: The sequence was designed and synthesized.

<400> SEQUENCE: 18

Cys Pro Ser Thr His Trp Lys
1               5

<210> SEQ ID NO 19
<211> LENGTH: 7
<212> TYPE: PRT
<213> ORGANISM: Artificial Sequence
<220> FEATURE:
<223> OTHER INFORMATION: The sequence was designed and synthesized.

<400> SEQUENCE: 19

Asn Val Gln Tyr Phe Ala Val
1               5

<210> SEQ ID NO 20
<211> LENGTH: 7
<212> TYPE: PRT
<213> ORGANISM: Artificial Sequence
<220> FEATURE:
<223> OTHER INFORMATION: The sequence was designed and synthesized.

<400> SEQUENCE: 20

Ala Ser His Thr Gln Lys Ser
1               5

<210> SEQ ID NO 21
<211> LENGTH: 7
<212> TYPE: PRT
<213> ORGANISM: Artificial Sequence
<220> FEATURE:
<223> OTHER INFORMATION: The sequence was designed and synthesized.

<400> SEQUENCE: 21

Thr Asn Ile Glu Ser Leu Lys
1               5

<210> SEQ ID NO 22
<211> LENGTH: 7
<212> TYPE: PRT
<213> ORGANISM: Artificial Sequence
<220> FEATURE:
<223> OTHER INFORMATION: The sequence was designed and synthesized.

<400> SEQUENCE: 22

Asn Cys His Lys Cys Trp Asn
```

```
<210> SEQ ID NO 23
<211> LENGTH: 7
<212> TYPE: PRT
<213> ORGANISM: Artificial Sequence
<220> FEATURE:
<223> OTHER INFORMATION: The sequence was designed and synthesized.

<400> SEQUENCE: 23

Ser His Leu Ser Lys Asn Phe
1               5
```

COMPOSITIONS AND METHODS FOR INCREASING THE IMMUNOGLOBULIN BINDING CAPACITIES OF IMMUNOGLOBULIN-BINDING POLYPEPTIDES AND OLIGOPEPTIDES

RELATED APPLICATION

The present application is a continuation of international application PCT/EP2017/082282 filed Dec. 11, 2017, entitled "Compositions and Methods for Increasing the Immunoglobulin Binding Capacities of Immunoglobulin-Binding Polypeptides and Oligopeptides", inventors Rajiv Datar, Carole Lainé, and Kajal Arora which is related to and claims the benefit of provisional application Ser. No. 62/432,807 filed Dec. 12, 2016, entitled, "Compositions and Methods for Increasing the Immunoglobulin Binding Capacities of Immunoglobulin-Binding Polypeptides and Oligopeptides," inventors Rajiv Datar and Carole Marie Lain&.

SEQUENCE LISTING

The sequence listing material in computer readable form ASCII text file (41 kilobytes) created May 16, 2019 entitled "01018-005_SequListing", containing sequence listings numbers 1-23, has been electronically filed herewith and is incorporated by reference herein in its entirety.

TECHNICAL FIELD

Compositions and methods of use are provided for derivatives of full-length or truncated forms of Protein A in combination with IgG-binding oligopeptides.

BACKGROUND

The number of monoclonal antibody (MAb) drugs continues to grow. In 2008, MAbs generated revenues in excess of US$15 billion (Leavy O. 2010. Nat. Rev. Immunol. 10: 297), making them the highest earning category of all biotherapeutics. The world MAb market will reach $62.3 billion in 2015, with next-generation therapeutic antibody revenues reaching $2.3 billion in 2015 according to Visiongain reports published in September and November 2011 (Visiongain 2011. London. UK, www.visiongain.com/Report/685/Therapeutic-Monoclonal-Antibodies-World-Market-2011-2021; Visiongain 2011. London, UK; www.visiongain.com/Report/712/Next-Generation-Antibody-Therapies-Pipeline-and-Market-2011-2021). Biosimilar antibodies will also begin to enter established markets as regulatory authorities clear approval pathways for them. Most antibody drugs treat cancer and autoimmune diseases, and many others are used to treat orphan and infectious diseases. Unfortunately, antibodies are complex proteins in a variety of parameters, which complicates their purification and characterization, making it difficult for their developers to meet the rigid requirements for therapeutics.

Because of both the natural and engineered variations in therapeutic antibody structures, there is no "one-size-fits-all" when it comes to techniques for MAb purification. The method that most closely approximates universal use is Protein A affinity chromatography, which has become the workhorse for antibody production. However, Protein A is expensive (with costs an order of magnitude over conventional chromatography resins), susceptible to degradation by proteases (cleaved domains can adhere to a MAb product, problems that complicate separations) (Carter-Franklin, J N et al. 2007. J. Chromatogr. A 1163, 2007 105-111), and is not fully stable to column washing and elution conditions. Further, Protein A generates an immunomodulation response and has limited capacity to accommodate the increasingly high titers found in modern upstream feeds.

Although the antibody purification field is advanced, among companies involved there has been some reluctance to invest in and introduce new technologies and/or further advance purification technologies. New alternatives have been described as "disruptive" (Low, D et al. 2007. J. Chromatog. B 848(1) S48-S63) predicting that Protein A will continue to be used for commercial-scale MAb purification throughout the foreseeable future (Low, D et al. 2007. J. Chromatog. B 848(1) S48-S63; Shukla, A A et al. 2007. J. Chromatogr. B 848(1) S28-S39). There is a need in the industry to lower production costs and pass along those savings by making medications more affordable for patients. The emergence of biosimilars (or follow-on biologics) and a growing number of companies seeking to capitalize on such products creates a need for new approaches for IgG purification (Gagnon, P. 2012. J. Chromatogr. A 1221, 57-70).

SUMMARY OF THE EMBODIMENTS

An aspect of the invention herein provides an engineered polypeptide that binds immunoglobulins or immunoglobulin-containing compounds, the polypeptide comprising at least one functional moiety of at least one naturally occurring or recombinant immunoglobulin binding protein selected from the group of a protein A, a protein G, a protein A/G, a protein L, and other immunoglobulin binding proteins, and a functional variant or portion thereof, the polypeptide being chemically conjugated or genetically fused with at least one synthetic functional immunoglobulin binding oligopeptide at a terminal amino acid residue or to an internal residue such as an internal lysine of the binding protein.

For example, the polypeptide contains a plurality of the functional moieties from the group and/or iterations of one of the functional binding protein moieties. The polypeptide in another embodiment further contains at least one linking element connecting at least two functional moieties. For example, the linking element has an amino acid sequence and contains fewer than about 1800 amino acids, or fewer than about ninety-five amino acids. For example, the linking element contains from about two to about fifty-four amino acids, or from about four to about ten amino acids.

In an embodiment of the polypeptide, the binding protein functional moiety has an amino acid sequence selected from the group of: SEQ ID NOs: 1, 2, 3, 4, 5, 6, 7, 11, 14, 15, and 17, and functional variants and portions thereof. In an embodiment of the polypeptide, the oligopeptide is selected from at least one of: amino acid sequence of: SEQ ID NOs: 8-10 and 18-23; functional variants and portions of these amino acid sequences; iterations having multiple copies of the sequences; and functional conservative amino acid substitutions of these sequences.

In various embodiments of the polypeptide, the functional moieties being chosen for binding targeted classes of IgG immunoglobulins or immunoglobulin-containing compounds, the polypeptide further contains a separation matrix medium in a large capacity capture bed that is characterized by fast flow rate kinetics.

In an engineered polypeptide that binds immunoglobulins or immunoglobulin-containing compounds, the polypeptide containing at least one functional moiety of a naturally occurring or a recombinant immunoglobulin binding protein or oligopeptide selected from the group of a protein A, a protein G, a protein A/G, a protein L, and other Ig binding proteins, and a functional variant or portion thereof, the improvement contains: at least one copy of the amino acid sequence or a portion thereof of the functional moiety or the functional variant or portion thereof, and further comprising at least one oligopeptide chemically conjugated to or genetically fused to a terminal amino acid residue or conjugated to or fused to within an internal reside such as an internal lysine.

An aspect of the invention provides a separation matrix that includes a polypeptide as described herein, coupled to a solid support. For example, the solid support preferably comprises a medical-grade porous polyvinyl chloride (PVC) medium having a form selected from the group of beads and sheets. In other examples, the PVC medium is embedded with or constitutes porous protein-adsorptive support surfaces, the medium having a bi-modal pore size distribution with the larger pore size ranging in average from about 0.5-5.0 micrometers and the smaller pore size ranging in average from about 0.003-0.3 micrometers. In various embodiments, the support surfaces material is selected from the group consisting of cellulose, agarose, nylon, porous metalloid oxides, porous metallic oxides, and porous mixed metallic oxides, silica particles, silica gel, controlled pore glass, alumina, stannia, titania, and zirconia. In various embodiments, the polypeptide and the solid support and the support surfaces material are coupled by single-point attachment. Alternatively, the separation matrix is generally the solid support and the support surfaces material are coupled by multi-point attachment.

The separation matrix aspects of the invention provided herein have very high binding capacities, for example, the immunoglobulin binding capacity of the polypeptide in mg per ml of bed volume is at least about 25, at least about 50, at least about 75. Further, the separation matrix has a scale up capacity which is linear and reproducible over a scale-up factor increase of at least about 500-fold, 1000-fold, 2000 fold, or at least about 3000-fold. The separation matrix in various embodiments includes at least one linker for attachment to at least one of the solid support and the support surfaces material. In general, the linker is selected from an amino acid sequence, a random amino acid polymer, a polyethylene glycol, covalently attached chemically or by genetic fusion to the polypeptide.

An aspect of the invention provides a composition comprising an oligopeptide having amino acid sequence selected from the group of: QPQMSHM (SEQ ID NO: 9); KPGKEDNN (SEQ ID NO: 10); CPSTHWK (SEQ ID NO: 18); NVQYFAV (SEQ ID NO: 19); ASHTQKS (SEQ ID NO: 20); TNIESLK (SEQ ID NO: 21); NCHKCWN (SEQ ID NO: 22); and, SHLSKNF (SEQ ID NO: 23). For example, an aspect of the invention provides a polypeptide having an amino acid sequence according to SEQ ID NO: 16 or 17. Various embodiments include an amino acid sequence which is 85% identical, 90% identical, 95% identical or 98% identical. Other embodiments include a polypeptide or a protein containing at least one copy of any of these oligopeptides. Still other embodiments include a chromatographic medium containing any of the oligopeptide or polypeptides compositions herein affixed to a support selected from the group of: a resin, a membrane, a filter, and a bead. These compositions include any with a change of up to 15% in amino acid sequence, resulting from one or more changes including due to deletion, an addition, or a conservative substitution.

An aspect of the invention provides a method of purifying an immunoglobulin from a biological sample, the method including steps of: contacting the sample to a separation matrix having a polypeptide as described herein, under conditions of ionic strength and pH for binding the immunoglobulins selectively and specifically to the matrix and passing other sample components into a flow through; and optionally washing the column and eluting the bound immunoglobulins from the matrix with an eluant buffer containing selected from the group characterized by in comparison to a loading buffer: decreased pH, increased pH, increased ionic strength, and presence of a competitive binding ligand, thereby purifying the immunoglobulin.

In an embodiment of this method, the separation matrix consists of a polypeptide, or a plurality of polypeptides, each of which includes at least one or a plurality of the oligopeptides, the respective polypeptides and oligopeptides being non-identical and having non-identical affinities for classes of immunoglobulins, and the method further includes purifying at least one or a plurality of antibody types selected from the group of: $IgG_1$, $IgG_2$, $IgG_3$, $IgG_4$, IgM, IgA, IgE and IgD. In alternative embodiments, the method further includes purifying selectively only IgG species, for example, one or more of all of the antibody types $IgG_1$, $IgG_2$, $IgG_3$, and $IgG_4$.

BRIEF DESCRIPTION OF THE DRAWINGS

FIG. 1 is a schematic map of native Protein A domains, including the N-terminal end of the Protein A chain 1, with the signal sequence, 2, followed by the five IgG binding domains of E, D, A, B and C. The C-terminal half of the Protein A molecule consists of the X-domain, and the sortase-recognition motif, 3, and a hydrophobic region, 4.

FIG. 2 is an amino acid sequence (SEQ ID NO:1) of native *Staphylococcus aureus* (NCTC strain 8325-4) Protein A (Lofdahl, S et al. 1983. Proc. Natl. Acad. Sci. USA 80, 697-701). N-terminal underlined sequence represents *S. aureus* signal peptide. C-terminal underlined sequence represents the X-domain.

FIG. 3 shows amino acid Protein A sequences of functional domains: IgG binding E domain (SEQ ID NO:2), IgG binding D domain (SEQ ID NO:3), IgG binding A domain (SEQ ID NO:4), IgG binding B domain (SEQ ID NO:5), IgG binding C domain (SEQ ID NO: 6) and X domain (SEQ ID NO:7). The X domain, SEQ ID NO: 7, in the underlined segment contains 12 repeated octapeptide units having amino acid sequence KPGKEDNN (SEQ ID NO:10) or variants of the two residues on the right which are NN for five of these repeats, and are NK or GN among the other repeats of the X region of SEQ ID NO: 7.

FIG. 4A is a schematic drawing of the structure formed by natural amino acids or by a combination of natural and unnatural amino acids having specific length "n" creating a linear polypeptide 5. The length of a linker comprising amino acid chain can be from one single amino acid up to 1,800 amino acids or more.

FIG. 9 is a graphical representation of the data in Table 5, showing unexpected linearity of scale up over a range of at least three orders of magnitude, of binding of IgG as a function of the bed volume, using the methods and compositions herein. At the very low end of the X-axis the bed volume is 4 mL. At the high end, the bed volume is 10,458 mL. The scale-up factor with respect to the bed volume is 2,615-fold. At the low end, the quantity of IgG bound is 0.1 g, while at the upper end it is 264 g, yielding a scale up capability which is at least a factor of 2,640-fold. Examples with even greater bed volumes, double the high end, follow the same extent of linearity of scale-up.

FIG. 10 is an amino acid sequence, SEQ ID NO: 11, of a Protein A derivative engineered herein which was designed for production by cytosolic expression. The gene encoding this amino acid sequence was engineered to remove the portion encoding the 36 amino acid leader sequence shown underlined at the amino terminus in FIG. 2, and further engineered to remove genetic material encoding additional carboxy terminus 31 amino acids, resulting in expression of the protein within the producing cells. The gene encoding the amino acid sequence was designed with codons optimized for *E. coli*, was synthesized, and the sequence was verified by restriction enzyme analysis. Genes were cloned in a commercially available standard vector.

FIG. 11 is an amino acid sequence, SEQ ID NO: 12, of a Protein A derivative engineered herein that was designed for bacterial periplasmic expression. The gene encoding SEQ ID NO: 12 was further engineered from that encoding SEQ ID: 11 to have a 20 amino acid amino terminus leader signal sequence causing the resulting Protein A derivative to be secreted into the periplasmic space and retained there. The gene encoding the amino acid sequence was designed with codons optimized for *E. coli*, was synthesized, and the sequence was verified by restriction enzyme analysis. Genes were cloned in the standard vector as described herein.

FIG. 12 is an amino acid sequence, SEQ ID NO: 13, of a Protein A derivative engineered herein which has been designed for extracellular expression, and contains the full leader sequence of native *S. aureus* Protein A shown in FIG. 2, and lacks the additional carboxy terminus 31 amino acids of FIG. 10. The gene encoding the amino acid sequence was designed with codons optimized for *E. coli*, was synthesized, and the sequence was verified by restriction enzyme analysis. Genes were cloned in the standard vector.

FIG. 13 displays amino acid sequences of two engineered versions of Protein A. A deleted version was designed having 415 amino acid residues, SEQ ID No: 14, and was constructed to remove the native signal sequence and to remove 35 amino acids from the carboxy terminus, and having a methionine initiating reside at the amino terminus. A 450 amino acid version, SEQ ID NO: 15, contains the *S. aureus* Protein A signal sequence to direct secretion and processing during production. The vertical bars between residues 327 and 328, and 332 and 333, respectively, indicate respective insertion points for design and construction of two engineered Protein A derivatives that contain oligopeptides and linkers inserted into the respective locations. The engineered polypeptide BIG_Hep4_lin1opt4_ExC having amino acid sequence SEQ ID NO: 16 was constructed by insertion between the amino acid residues 327 and 328, and BIG_Hep4_lin3opt4_ExC amino acid sequence SEQ ID NO: was constructed by insertion between 332 and 333.

FIG. 14 displays amino acid sequences of designed and synthesized Protein A derivatives containing inserts of linker sequences and multiple copies of engineered heptapeptide iterations of SEQ ID NO: 9, the protein being engineered for enhanced binding of immunoglobulins. Construct BIG_Hep4_lin1opt4_ExC amino acid sequence SEQ ID NO: 16, 543 amino acids, contains an insert displayed with a gray highlight, from residue 333 to residue 425 with the designed linker and three embedded heptapeptide iterations, each having the amino acid sequence QPQMSHM (SEQ ID NO:9) shown in dark rectangles. Construct BIG_Hep4_lin3opt4_ExC amino acid sequence SEQ ID NO: 17, 533 amino acids, contains an insert from reside 328 to reside 410 with the designed linker and the three embedded heptapeptide iterations similarly indicated.

DETAILED DESCRIPTION

Figures 4B, 5:
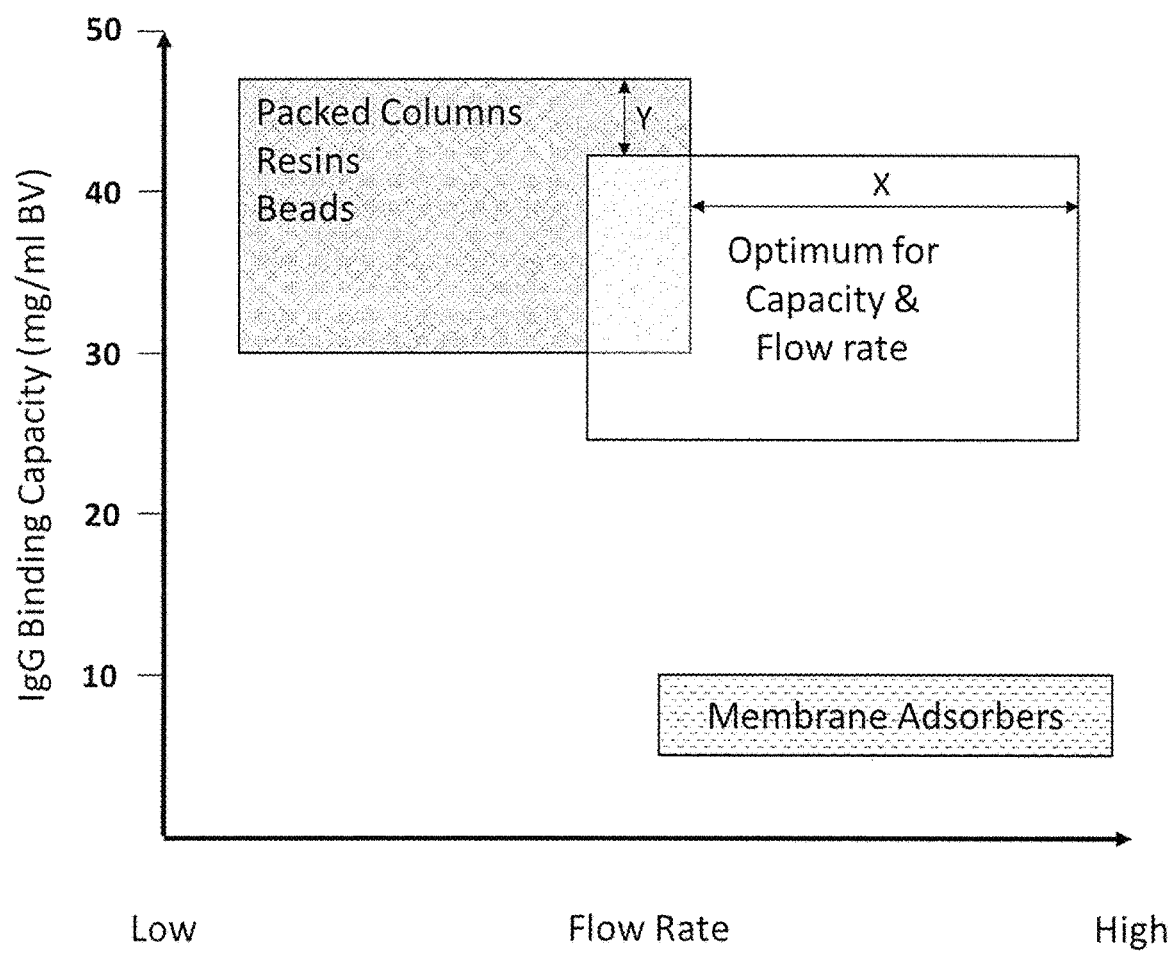
FIG. 4B are amino acid sequences of exemplary oligopeptides that have affinity to bind IgG protein. These oligopeptides can be engineered into longer proteins as monomeric units (single copy), or can be linked together to form longer chain polypeptides, or scattered at recommended positions in a protein in any manner or combination, for example with the elements shown in FIG. 3. It is known that Protein A, for example, does not bind human $IgG_3$ (see Table 2 which shows that Protein A binds differentially to immunoglobulins IgG and IgM, and differentially to subclasses of IgG from humans, and from other mammalian species). Such peptides can confer additional specificity to various embodiments of the protein-polypeptide or polypeptide-polypeptide moieties, which are the subject of this invention, to engineer for capture of a broader range of immunoglobulins in one step.
FIG. 5 is a graphical representation of IgG binding capacity (ordinate) as a function of flow rate (abscissa). The upper left hand quadrant depicts the operational range for prior art packed columns containing chromatography resins or beads, and the lower right hand quadrant shows the operational area for membrane adsorbers. The ideal area to optimize capacity and speed is shown in FIG. 5. The difference in the "Y" component between optimum technology exceeds the difference in the "X" component offered by the packed column technologies.

Protein A: Protein A is a 42-kDa protein anchored in the cell wall of *Staphylococcus aureus* (Sjöquist. J et al. 1972. Eur. J. Biochem. 30(1) 190-194) with the ability to selectively interact with immunoglobulins (IgGs) (Langone, J J. 1982. Adv. Immunol. 32, 157-252). It binds strongly to all classes of human IgGs except for $IgG_3$ (Langone, J J supra). Full-length Protein A consists of five homologous domains (referred to as E, D, A, B, and C, in order of their arrangement from the N-terminus) and one cell-wall-associated domain (Lofdahl et al. 1983 supra; Guss, B, et al. 1984. Eur. J. Biochem. 138(2) 413-420). Protein A was initially produced by culturing the Cowan strain of *S. aureus* and extracting the protein from the bacterial cell walls (Sjöquist, J et al. 1972. Eur. J. Biochem. 29(3) 572-578). The sequence of native *S. aureus* Protein A is shown in FIG. 2 (SEQ ID NO: 1). A strain of *S. aureus* was later discovered that secretes Protein A into its culture supernatant (Lindmark, R et al. 1977. Eur. J. Biochem. 74(3) 623-628). As recombinant DNA technology advanced, Protein A was expressed as a fragment without its cell-wall domain using *Escherichia coli* as an expression host (Duggleby, C J et al. 1983. Nucl. Acids Res. 11(10) 3065-3076; Hammond, P M et al. 1990. Ann. NY Acad. Sci. 613, 863-867; Cai, S et al. 1992. Chin. J. Biotechnol. 8(2) 93-98; Engel, H et al. 1992. Prot. Expr. Purif. 3(2) 1992: 108-113). Various engineered derivatives of Protein A are shown in FIGS. 10-12, engineered to be expressed and to be located intracellularly, in periplasmic space, or extracellularly, respectively, in bacterial expression vectors and host cells.

IgG binds to Protein A at the IgG Fc region (Lindmark, R et al. 1983. J. Immunol. Meth. 62(1) 1983: 1-13; Gouda, H et al. 1998. Biochem. 37(1) 129-136). The interaction is very specific and hydrophobic in nature. It involves some hydrogen bonds and two salt bridges. The high specificity enables Protein A affinity chromatography to remove greater than 98% of impurities from complex solutions such as cell harvest media in a single purification step (Follman, D K et al. 2004. J. Chromatogr. A 1024: 79-85). One drawback of the well-known specificity of interaction of Protein A with IgGs is necessity of use of harsh conditions such as low pH for elution. That can be problematic for some antibodies that are either unstable or tend to aggregate at low pH levels. In general, only a small amount of impurities—e.g., aggregates, residual host-cell proteins, DNA, and leached Protein A—will remain after this single starting unit of downstream process operation. These remaining impurities usually are removed in one or two additional chromatography steps.

Affinity Supports: Protein A has been immobilized to a large number of types of supports suited for liquid chromatography of proteins (Boschetti, E et al. 2000. Academic Press: San Diego, Calif., 535; see Table 1). Initially, a popular product was Protein A immobilized on CNBr-activated Sepharose CL 4B from Amersham (now GE Healthcare) in Sweden. The medium was characterized as having high selectivity and low nonspecific adsorption, but due to the nature of the agarose-based support, a packed bed was too soft to allow for high flow rates. For this reason that medium has been largely replaced by more highly cross-linked Sepharose for large-scale applications. Modern Protein A sorbents are based on controlled porous glass, coated porous polymer gel-filled mineral materials, and other supports (Hahn, s R et al. 2003. J. Chromatogr. B 790 2003: 35-51) using materials sufficiently rigid to allow for column operation at high flow rates. Exemplary support materials are shown in EP2902094 published May 8, 2015, Laine, C.

State of the Art: Since the first reports over 40 years ago involving use of immobilized Protein A for affinity purification of antibodies (Hjelm, H et al. 1972. FEBS Lett. 28(1) 1972 73-76; Kronvall G. 1973. J. Immunol. 111(5) 1401-1406), it has become the industrial standard for purification of clinical-grade MAbs (Gagnon P. 1996. Validated Biosystems Inc.: Tucson, Ariz.). Janssen Biotech's Muromonab (brand-name Orthoclone OKT3) is a CD3-specific MAb that was approved by the US Food and Drug Administration (FDA) in 1986 (Becker. H. 2007. Handbook of Therapeutic Antibodies Volume III: Approved Therapeutics. Dubel S, Ed. Wiley-VCH: Weinheimn, Germany. 905-940) for use in treatment of acute transplant rejection, an early approved product made using Protein A as a capture step in its manufacturing process. Protein A capture serves as the key volume-reduction step in antibody downstream processing. The purification scheme for Protein A chromatography involves binding at neutral pH and elution at acidic pH. Ease of method development has caused Protein A affinity chromatography to be almost universally adopted in large-scale manufacturing processes, and almost universal applicability and the overall scheme of associated operating conditions lend themselves readily to a platform format (Shukla, A A et al. 2007. J. Chromatogr. B 848(1) S28-S39).

Economics: Cost is another very important factor as it relates to medical care costs. Some Protein A resins cost as much as $15,000/L. Table 1 shows prices from 2013, and it is expected that these are underestimates for current values. Even with larger numbers of players and increasing competition, prices continue to be quite high. Repligen resins cost about $6,000/L and tolerate only 0.1N NaOH. It has been argued that the main limitation of Protein A is capacity or productivity, rather than cost (Gagnon, P. 2012. J. Chromatogr. A 1221, 57-70), and that capacity issues result from use of porous particles in a fixed bed. The Protein A molecule per se occupies a large amount of intrapore space in porous media because of its size.

TABLE 1

Some commercially available Protein A sorbents for affinity chromatography

| Sorbent | Ligand | Manufacturer | Bead Matrix | Estimated Price* |
|---|---|---|---|---|
| CaptivA | Recombinant native Protein A | Repligen | 4% agarose 4FF | $5,800/L |
| MAbSelect Xtra | Recombinant Protein A | GE Healthcare | Highly cross-linked agarose | $12,803/L |
| MAbSelect SuRe | Tetramer alkali-stabilized Z-domain | GE Healthcare | Highly cross-linked agarose | $15,850/L |
| MAbSelect SuRe LX | Tetramer alkali-stabilized Z-domain | GE Healthcare | Highly cross-linked agarose | $17,157/L |
| Prosep Ultra Plus | Recombinant native Protein A | EMD Millipore | Controlled pore glass | $14,440/L |
| Poros MAb-Capture A | Recombint native Protein A | Life Technologies | Polystyrene divenyl-benzene | $13,750/L |
| TOYOPEARL AF-rProtein A-650F | Tetramer alkali-stabilized C domain | Tosoh Bioscience | Polymeth-acrylate | $12,240/L |

*2013 list prices in US dollars (from websites or direct sales inquiries) listed as fair comparison without discounts (e.g., for large-volume orders).

Other Chromatographic Methods: A significant amount of effort has gone into further developing one type of fluidized chromatography technique known as expanded-bed absorption (EBA). It involves the use of adsorbent particles dispersed in a liquid media. One main benefit of EBA is a reduction in the number of steps required for antibody recovery due to direct capture of product from a cell suspension. For antibodies, however, this application could not replace Protein A, which in a form bonded to agarose is used to capture the antibody in EBA.

Membrane adsorbers ("membrane chromatography") offer clear advantages over conventional resins, both in terms of disposability (which eliminates the need for cleaning and validation) and the ability to operate at high flow rates. Because of their lower surface area, however, most membrane adsorbers suffer from low binding capacity compared with an equivalent volume of porous particles. An exception to that limitation is membrane technology for example, developed by Natrix Bioseparations (Kuczewski M, et al. 2011. Biotechnol. J. 6(1) 56-65), with membranes that consist of a polymeric hydrogel formed within a flexible porous support matrix. That macroporous hydrogel polymer structure provides high binding-site density and a large surface area for binding and rapid mass transfer.

Kuczweski et al. supra developed a membrane-based, high-capacity, cation-exchange capture step for MAbs using a C membrane from Natrix. They reported a capacity of 55 mg of antibody per milliliter of membrane, which is about five times that of other membrane adsorbers (Gottschalk, U. 2005. Biopharm Int. 18 (6): 42-58). Table 3 shows binding capacities of some commercially available Protein A sorbents, in a range from 30 mg/mL to 45 mg/mL. Because of low capacities and dilutions created by the void volume and variations in membrane thickness, most of these adsorbers are preferentially used in flow-through mode.

The words, "protein", "polypeptide" and "oligopeptide" as used herein all refer to polymers of amino acids. The amino acids are generally L-amino acids, and may be naturally occurring or non-naturally occurring. Generally a protein refers to a biologically expressed product found in correct conformation with respect to secondary, tertiary and quaternary structures. In contrast, the term "oligopeptide" refers to a short polymer, at least about four amino acids in length, generally less than about 50 amino acids in length, which has been synthesized by standard procedures using solid phase initiating residues and F-moc or T-boc protected reagents. The oligopeptides herein are useful individually as ligands for various target proteins, and are envisioned herein as moieties of a larger polypeptide in combination with one or more domains that are subsequences of naturally occurring proteins having affinity for immunoglobulins.

The term, "polypeptide" as used herein and in the claims designates a moiety which is generally designed, although it may contain naturally occurring amino acid sequences, and may be produced by peptide synthesis or produced recombinantly in transformed or transfected cells. A polypeptide is generally longer than an oligopeptide, for example, may be a polymer of several hundred amino acids. The useful compositions herein are designed and are recombinantly expressed from a synthetic gene encoding the polypeptide, or are chemically engineered by standard chemical coupling procedures. The polypeptides contain one or more subcomponent amino acid sequences so that both naturally occurring and synthetic designed novel amino acid sequences are, in various embodiments of the polypeptide, present in various functional portions of the polypeptides.

The term polypeptide is used to distinguish this designed binding material from its targets, which are referred to herein as proteins as these are members of the immunoglobulin family. The target proteins can be made in vivo in a vertebrate animal and obtained from blood or serum, or can be produced in cultures from genetically engineered cells, e.g., expressed from recombinantly prepared vectors and cell lines in cell culture. In general the target proteins are oligomeric and are in native conformation. However target proteins include single chain immunoglobulin derivatives that are engineered from antibody proteins, including immunoglobulins that are the result of protein engineering and were isolated from mutagenized libraries of display vectors.

The designed and synthesized polypeptides of the invention herein can be genetically encoded and biologically expressed by a cell transformed or transfected with a vector containing an encoding gene. The choices in design of the polypeptide of types of components, and number of iterations of each of the components present in the polypeptide, is determined by the user, and the binding functions of each of the candidate polypeptides are determined with assays of affinity for each of a plurality of desired target immunoglobulins, and selection for those candidates with an optimum extent of affinity and a desired pattern of affinities for each among the classes of immunoglobulins.

Protein A is a 42 kDa surface protein originally found in the cell wall of the bacteria *Staphylococcus aureus*. It is encoded by the SpA gene. It has found extensive use in biochemical research and in the production of biological drugs because of its ability to bind immunoglobulins (IgG). It is composed of five homologous Ig-binding domains that fold into a three-helix bundle (see FIG. 1). Amino acid sequences of the intact, native *Staphylococcus aureus* Protein A is shown in FIG. 2, while the amino acid sequences of the five individual Ig-binding domains and the anchoring region is shown in FIG. 3. Each domain is able to bind proteins from many mammalian species, most notably IgGs (see Table 2). It binds the heavy chain within the Fc region of most immunoglobulins and also within the Fab region in the case of the human VH3 family (Ljunberg et al., 1993).

TABLE 2

(A) Immunoglobulin affinity for recombinant Protein A

| Species | Immunoglobulin | Type | Subclasses | Strength |
| --- | --- | --- | --- | --- |
| Human | IgG | | 1, 2, 4 | |
| | IgA | | 2 | |
| | IgM | Some | — | |
| Rabbit | IgG | Soluble complex | — | |
| Mouse | IgM | | | Weakly |
| | IgG | | 1 | Weakly 2a, 2b, 3 |
| Guinea Pig | IgG | | 1, 2 | |
| Rat | IgG | | 1, 2c | Weakly |
| Cow | IgG | | 2 | Weakly |
| Sheep | IgG | | 2 | Weakly |
| Goat | IgG | | 2 | Weakly |
| Dog | IgG | | a, b, c, d | |
| | IgA | Some | | |
| | IgM | Some | | |

(B) Comparison of species specific immunoglobulin binding to Protein A and protein G

| Immunoglobulin | Protein A | Protein G |
| --- | --- | --- |
| Human | Strong | Strong |
| Rabbit | Strong | Strong |

TABLE 2-continued

| | | |
|---|---|---|
| Mouse | Medium | Strong |
| Guinea Pig | Medium | Strong |
| Rat | Weak | Medium |
| Cow | Weak | Strong |
| Sheep | Weak | Strong |
| Goat | Weak | Strong |
| Horse | Weak | Strong |

Recombinant Staphylococcal Protein A (SpA) is often produced in E. coli for use in immunology and other biological research. Protein A has variously been coupled to other molecules including a fluorescent dye, enzymes, biotin, colloidal gold or radioactive iodine without affecting the antibody binding site. Protein A is also widely utilized coupled to magnetic, latex, agarose beads and a host of other media.

Protein A is often immobilized onto a solid support and used as a reliable method for purifying total IgG from crude protein mixtures such as from serum, ascites fluid, fermentation- or bioreactor broths, or coupled with markers to detect the presence of antibodies. Immunoprecipitation studies with Protein A conjugated to beads are also commonly used to purify proteins or protein complexes indirectly through antibodies against the protein or protein complex of interest.

Because of the ability of Protein A to bind a large variety of IgGs, one of its most important uses is in the affinity chromatographic purification of antibodies and antibody fragments. Immunoglobulins represent the most prevalent biopharmaceutical products in either manufacture or development worldwide. The high commercial demand for and hence value of this particular therapeutic market has led to the emphasis being placed on pharmaceutical companies to maximize the productivity of their respective monoclonal antibody (MAb) manufacturing processes whilst controlling the associated costs.

Affinity chromatography is used in most cases, as one of the key steps in the purification of these immunoglobulin molecules, such as monoclonal or polyclonal antibodies. At present, SpA-based affinity medium probably is the most widely used affinity medium for isolation of monoclonal antibodies and their fragments from a variety of different industrial feed stocks from cell cultures. Accordingly, various matrices and resins comprising Protein A-ligands are commercially available, for example, in the form of native Protein A (e.g. Protein A SEPHAROSE™, GE Healthcare, Uppsala, Sweden), or containing recombinant Protein A (e.g. rProtein A SEPHAROSE™, GE Healthcare).

Major drawbacks of Protein A include the fact that it is expensive and unstable under typical column cleaning/sanitization conditions such as 1 M NaOH (Costioli, M et al., 2010 Biopharm International 23 (6); Gagnon, P. 2012 J. Chromatogr A 1221: 57-70).

Derivatives of Protein A have been shown to retain similar binding properties while showing an increase either in binding capacity or stability (Gulich, S et al., 2002 Protein Eng 15 (10): 835-842; Linhult, M et al., 2004 Proteins 55 (2): 407-416). A few alkaline-stabilized Protein A derivatives are currently marketed as chromatography resins such as the GE Healthcare (Pittsburgh, Pa., USA) MAbSelect Sure™ resin which uses a modified tetrameric B binding domain, Protein A ceramic Hyper D F resin from Pall Corporation (Port Washington, N.Y., USA) and Tosoh Biosciences (South San Francisco, Calif., USA) Toyopearl AF-Protein A-650F resin, which uses a tetrameric derivative of the C binding domain of Protein A.

However, Protein A derivatives still suffer from high costs associated with licensing fees and costs of producing and purifying the recombinant protein. This purification comes with an extremely high price tag (see Table 1). The price of Protein A resins can be as high as $17,000 or more per liter of the resin. This high cost adds directly to the cost-of-goods factor in the production of biological drugs.

To decrease the operating and replacement costs of Protein A affinity chromatography media, there is a need in the bioprocessing industry for Protein A media that can be used with increased number of cycles than are now available.

Modifications to the Protein A molecule, which have involved the sequencing and working with specific domains from within the Protein A molecule have been carried out to increase its binding capacity, but these have resulted only in incremental improvements (see Table 3).

TABLE 3

Immunoglobulin binding capacities of some commercially available Protein A sorbents.

| Sorbent | Ligand | Manufacturer | Bead Matrix | DBC at 3 min Residence* |
|---|---|---|---|---|
| CaptivA | Recombinant native Protein A | Repligen | 4% agarose 4FF | ~38 mg/mL |
| MAbSelect Xtra | Recombinant Protein A | GE Healthcare | Highly cross-linked agarose | 35 mg/mL |
| MAbSelect SuRe | Tetramer alkali-stabilized Z-domain | GE Healthcare | Highly cross-linked agarose | ≥30 mg/mL |
| MAbSelect SuRe LX | Tetramer alkali-stabilized Z-domain | GE Healthcare | Highly cross-linked agarose | 45 mg/mL |
| Prosep Ultra Plus | Recombinant native Protein A | EMD Millipore | Controlled pore glass | ~48 mg/mL |
| Poros MAb-Capture A | Recombint native Protein A | Life Technologies | Polystyrene divenyl-benzene | >45 mg/mL |
| TOYOPEARL AF-rProtein A-650F | Tetramer alkali-stabilized C domain | Tosoh Bioscience | Polymeth-acrylate | >30 mg/mL |

*DBC: Dynamic Binding Capacity at a particular residence time. From websites and sales literature.

Mutated immunoglobulin-binding proteins having an Asn residue mutated to an amino acid other than Gin or Asp (using the three letter amino acid code) are shown in patent application WO2003080655A1 published Oct. 2, 2003, inventor Hober, S. et al., and were found to have increased chemical stability at high pH. Hall et al. in WO2008039141 published Apr. 3, 2008 showed that domain C of Protein A withstands harsh cleaning agents. Nakamura, S. et al. produced a protein having an amino acid sequence ATK or ASK (using the one letter amino acid code) to be used for isolating immunoglobulins in WO2012086660A1 published Jun. 28, 2012. Bjoerkman et al. WO2012087231 published Dec. 20, 2010, produced an affinity chromatography matrix with one or more ligands of Protein A domains having asn or his residues at the H18 of the B domain, and observed increased elution pH compared to non-substituted Protein A. Kihira, Y. et al. EP0863210 published Sep. 9, 1998 produced immunoglobulin-binding artificial protein having linked units. Caustic-stable chromatography ligands having two or more B or Z domains were found by Bian et al. to be alkali stable in EP2202310 published Jun. 30, 2010. Similarly, Yoshida et al. engineered acid stable Protein A by replacing G residues with amino acids other than A, in EP2412809 published Feb. 1, 2012. Novel Protein A-based ligands having a deletion of at least three amino acids with mutations at position 29 that replace G or A with K were observed by Spector et al. to reduce Fab binding, in EP2532672 published Dec. 12, 2012. The ability of short peptides of specific length "n" that might mimic the affinity binding characteristics of Protein A, have been explored (Yang et al., J. Pept. Res. 6: 120-137, 2006) in efforts to reduce the high cost of Protein A-based, large-scale affinity purifications (see FIG. 4).

The compositions provided herein are polypeptides that integrate the endogenous affinity characteristics of either the full-length or the truncated versions of Protein A, with the affinity characteristics of shorter oligopeptides, to dramatically enhance the IgG binding characteristics of the combined entity or entities. Such modifications are engineered either by design, synthesis, and ligation of genetically-fused nucleic acid moieties encoding full-length or truncated versions of recombinant Protein A and the oligopeptides, including possible peptide linkers for display of the high binding oligopeptides on outer surfaces of the designed polypeptides, or are engineered by chemical conjugation of these entities.

There are serious cost drawbacks to using existing forms of Protein A, bound to either resins or membrane supports to purify high-value, life-saving biological drugs. Downstream purification of these MAbs can account for almost 80% of the total cost of manufacturing (Gottschalk, U. 2005. Biopharm Int. 18 (6): 42-58), while purification costs with Protein A can amount to in excess of 40% of the total purification cost, suggesting opportunities for novel antibody purification technology.

There continues to be a need in this field to obtain protein ligands bound to a separation matrix that is able to optimize an increased binding capacity with an increased flow rate.

This invention, by its ability to substantially increase the "binding capacity-flow rate" combination paradigm of Protein A-based moieties (see FIG. 5), can dramatically reduce the cost of affinity purification, thereby reducing the cost-of-goods factor in the overall cost of high-value biological drugs.

Embodiments of the invention herein provide the use of methods for increasing IgG binding capacity of IgG binding proteins and peptides such as, but not limited to Protein A-based moieties. Protein A affinity chromatography is a very effective capture step for monoclonal antibody (MAb) purification due to its high selectivity, enabling high purity and relatively high concentration in a single affinity chromatographic step. However, Protein A has characteristics that limits its utility during MAb purification. Native and recombinant Protein A are not stable under high alkaline conditions, as a result of which the ideal cleaning/sanitization solution, 1 M NaOH, cannot be used for Protein A cleaning (Jones, S C B et al. 2004. 3rd International Symposium on Downstream Processing of Genetically Engineered Antibodies and Related Molecules. Nice, France). Binding capacity of Protein A columns or Protein A membrane adsorbers is also limited by the kinetics of MAb-Protein A binding as well as the density of Protein A ligand obtainable (Saha, K et al. J. Anal. Chem. 75(4): 835-842; Sheth, B. Thesis. University College of London, 2009).

The production bottleneck with Protein A chromatography as a result of improved expression and production techniques, increasing yields of MAb titers have led to the need for ever larger Protein A columns and eventually expensive new hardware such as pumps and columns. Column diameters are limited by the footprint within existing plants (Palma, A D.2005. Cost-Drive Chromatograpy. www.pharmacueticalmanufacturing.com/articles/2005). Increasing the column height is impractical since pressure in the resin or separation medium increases with bed height and higher pressure either compresses the resin or damages the pumps (Thillaivinayagalingam, P et al. 2007. Genet. Eng. Biotechn. N. 27(11)). Increasing bio-reactor titers by increasing the number of chromatography cycles, increases both total processing time and resources and consequently the total cost. As seen in Table 5, binding capacity of PVD-Si-Protein A remains constant throughout a scale-up that ranges more than three orders of magnitude making large-scale antibody production more efficient and economical.

Protein A instability is a major cause of the Protein A chromatography bottleneck and high resin cost. This instability, particularly occurring during resin cleaning and sanitization, decreases the binding capacity over a number of cycles further lowering yields of the product throughput.

Small peptides have an advantage over larger ligands such as Protein A due to the much higher ligand density attainable on the pore surface (Yang, H et al. 2006. J. Pept. Res. 66: 120-137). On similar polymer porous beads as the Protein A resin MAbSelect®, MAb binding capacities on certain cation-exchange resins have reached over 100 mg/mL (Liu et al., 2011); though MAbSelect binding capacity is in the 30-45 mg/mL range, with typical 2-3 min column residence times (Ljunglöf, A et al. 2011. Bioprocess Int. 9(7): 66-67). Therefore, it is possible to bind MAb to a higher capacity than can be realized with Protein A resins prior to use of the engineered polypeptides herein. Table 4 shows data obtained in examples herein using recombinant Protein A or protein G ligands attached to porous PVC media embedded with silica particles. Different human serum antibody subclasses were observed to bind to each of these media to different extents. For example, PVC-Si-Protein A was observed to have preferentially bound $IgG_1$, $IgG_2$, $IgG_4$, IgM, IgA and IgE. In contrast, PVC-Si-Protein G was observed to bind four IgG subclasses but not IgM, IgA, IgE or IgD. Clearly the data in examples herein shown in FIG. 9 and Table 5 illustrate the non-identical and even unique affinities of each of Protein A and protein G to differentially bind eight types or subclasses of human immunoglobulins.

TABLE 4

Specificities of porous PVC media embedded with silica particles with recombinant Protein A and protein G ligands for human serum proteins

| Antibody Type | PVC-Si-Protein A | PVC-Si-Protein G |
|---|---|---|
| $IgG_1$ | + | + |
| $IgG_2$ | + | + |
| $IgG_3$ | − | + |
| $IgG_4$ | + | + |
| IgM | + | − |
| IgA | + | − |
| IgE | + | − |
| IgD | − | − |
| Albumin | − | − |

TABLE 5

Example of IgG binding capacity of porous PVC media embedded with silica particles with native recombinant Protein A ligand

| Bed Volume (mL) | Rabbit IgG Binding (g) | (mg/mL BV) |
|---|---|---|
| 4 | 0.10 | 25.0 |
| 10 | 0.26 | 26.0 |
| 16 | 0.4 | 25.0 |
| 40 | 1.0 | 25.0 |
| 61 | 1.6 | 26.2 |
| 152 | 4.0 | 26.3 |
| 150 | 4 | 26.7 |
| 374 | 10 | 26.7 |
| 615 | 16 | 26.0 |
| 1,539 | 40 | 26.0 |
| 4,183 | 108 | 25.8 |
| 10,458 | 264 | 25.2 |

In an alternative embodiment provided herein for purification media compositions and methods of making such media, small peptides are "grown" on- and/or from the pore surface of matrix material such as PVC-Si via surface-initiated polymerization. A potential for much higher peptide densities compared to Protein A is realized from surface polymerization methods, similar to other chemical ligands (Bhut et al., 2008. J. Membr. Sci. 325(1): 176-183). Additionally, small peptides have greater stability than larger polypeptides and proteins under sanitization conditions, particularly alkaline conditions, because small peptides lack easily disrupted secondary and tertiary structures, and these structures are more readily reassembled under original conditions. Nevertheless, a concern arising from use of smaller ligands is that they may not have the same range of specificity as the Protein A molecule itself. However, incorporating the smaller oligopeptides provide herein into full or truncated forms of Protein A, or other immunoglobulin-binding moieties, provides compositions having the potential for increasing capacity by working around the issues of steric hindrance.

Present processes, systems and hardware supporting Protein A based affinity purification, and the prohibitive cost of the Protein A ligand itself, are not amenable for single-use technologies. It is a particular focus and subject of this invention to optimize the above-mentioned limiting parameters of Protein A based affinity purification and to bring the potential of single-use Protein A based purification technology and products into reality.

Nucleic acid sequences encoding various combinations of domain polypeptides of SEQ ID NOs: 2-6 (FIG. 3) and the oligopeptides of SEQ ID NOs: 8-10 (FIG. 4B) were expressed to obtain the oligopeptides having the amino acid sequences in examples herein using display phage, by methods shown in U.S. Pat. No. 8,685,893, Sidhu et al., issued Apr. 1, 2014, and references cited therein. Resulting libraries of displayed sequences were enriched to select for improved optimized affinity to a target which is a class of immunoglobulin of choice, for example IgG₁. Positive selection was combined with a negative selection, to reduce affinity for unwanted immunoglobulins such as IgE.

A series of oligopeptides were obtained herein using these phage display methods, and candidate oligopeptides bound to phage were screened for ability to bind to the immunoglobin subtypes. Oligopeptides obtained by this method were all found to bind to all of the tested immunoglobin subtypes. These amino acid sequences include, using the one letter amino acid code: CPSTHWK (SEQ ID NO: 18); NVQYFAV (SEQ ID NO: 19); ASHTQKS (SEQ ID NO: 20); TNIESLK (SEQ ID NO: 21); NCHKCWN (SEQ ID NO: 22); and, SHLSKNF (SEQ ID NO: 23).

Among the oligopeptides tested for affinity to immunoglobulin protein subclasses, the oligopeptide of SEQ ID NO: 9 was observed to have the greatest affinity for binding to subtypes $IgG_1$ and $IgG_3$. Accordingly, this oligopeptide was selected for insertion, with linkers, into the designed and engineered Protein A derivative compositions herein.

Design and Synthesis of Protein A Polypeptides

Figure 6:
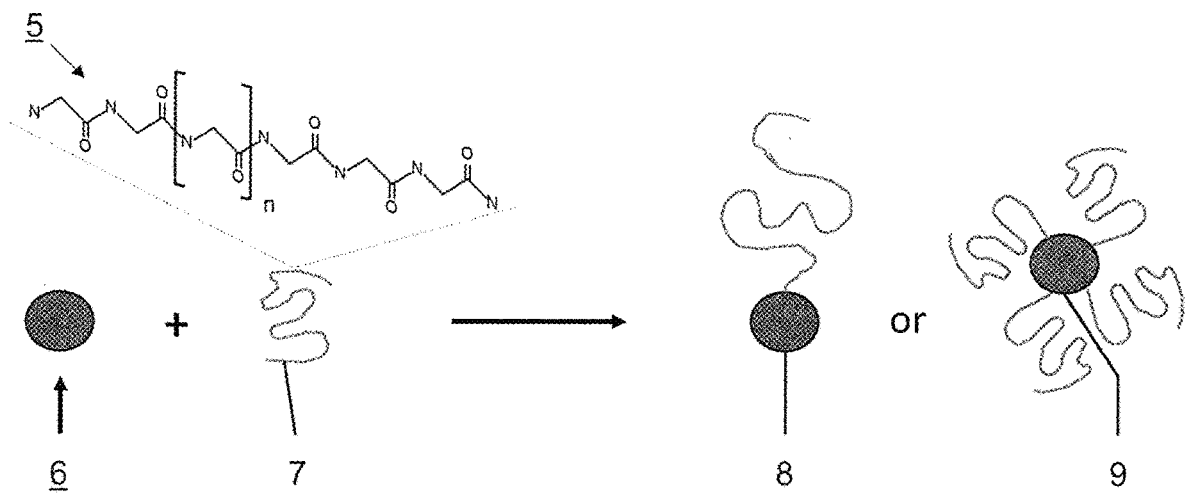
FIG. 6 shows schematic examples of various protein-polypeptide moiety or protein domain and oligopeptide combinations, respectively that are possible to engineer from among any of the five IgG binding domains, depicted as 6, and 7, respectively to form a variety of combinations, illustrated as 8 and 9.
Figure 7:
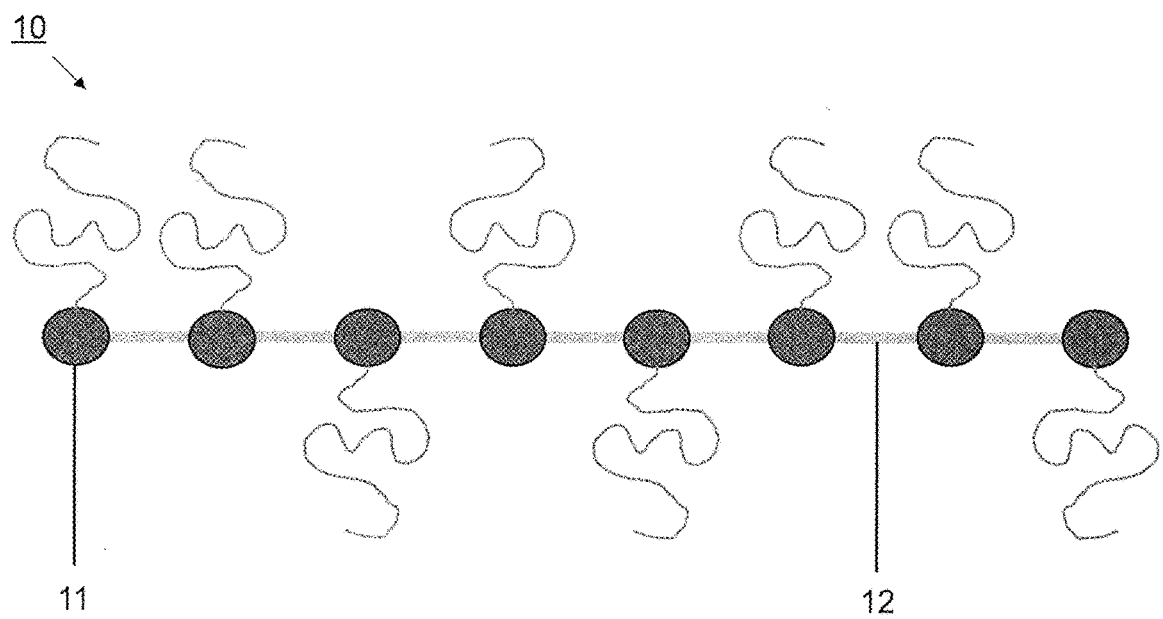
FIG. 7 is a schematic representative of IgG binding domains of Protein A—full length or truncated, linked to each other and to polypeptide moieties of FIGS. 4A-4B. The IgG binding domains of Protein A may be repeat units of one single domain (e.g. a sequential oligomer of domain E, for example, E-E-E- . . . , or such an oligomer interspersed with one or more oligopeptides or with linkers) or to any combination with each other as may be desired for a particular 1 gG binding effect.
Figure 8:
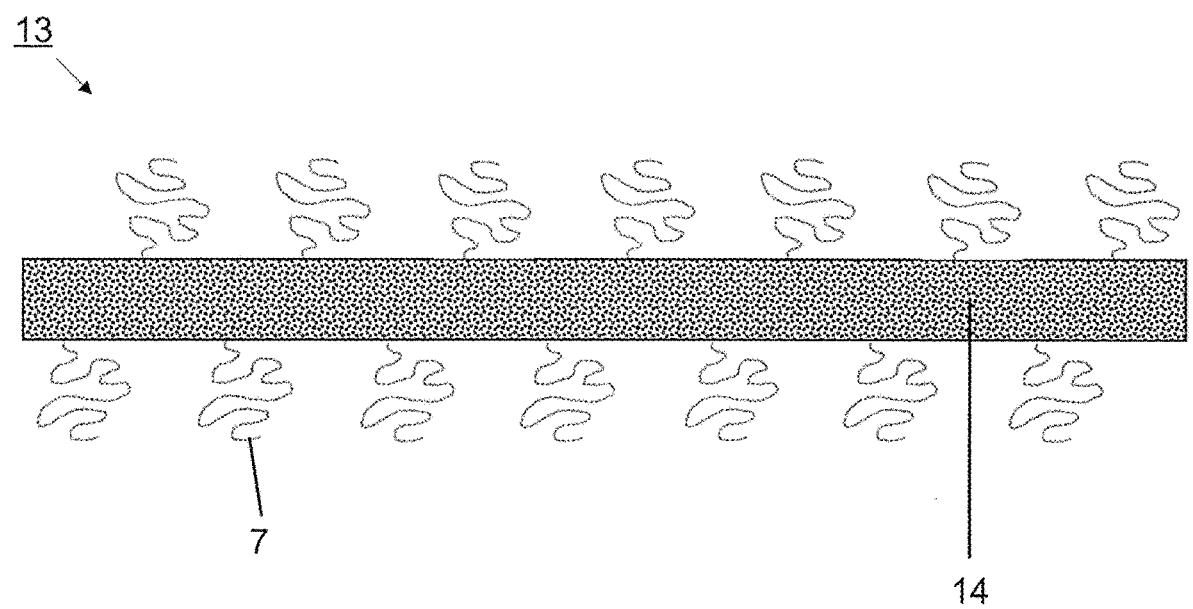
FIG. 8 is a depiction of polypeptides engineered herein, 7, bound to a support matrix as described here and in the claims. Support matrix 14 is a solid support or is porous in nature. The composition 7 can be attached to—or grown on and within the surfaces of the support matrix 14.

Two polypeptide amino acid sequence combinations of portions of Protein A with linkers and oligopeptide inserts were designed for testing expression, secretion and production in the context of pET30b+ (commercially available from EMD/Sigma/Millipore) plasmid backbone in transformed cells of *Escherichia coli*. Theoretical design considerations are shown FIG. 6, in which various protein-polypeptide moiety or protein domain and oligopeptide combinations, respectively illustrate possible engineered derivatives chosen from among any of the five IgG binding domains of Protein A. These may be further linked linearly, as illustrated in FIG. 7. In these drawings, high binding oligopeptide domains and linkers are shown as wavy lines, and the Protein A core is illustrated as a circle. These engineered Protein A compositions may be bound to a support matrix as shown in FIG. 8.

Figure 15:
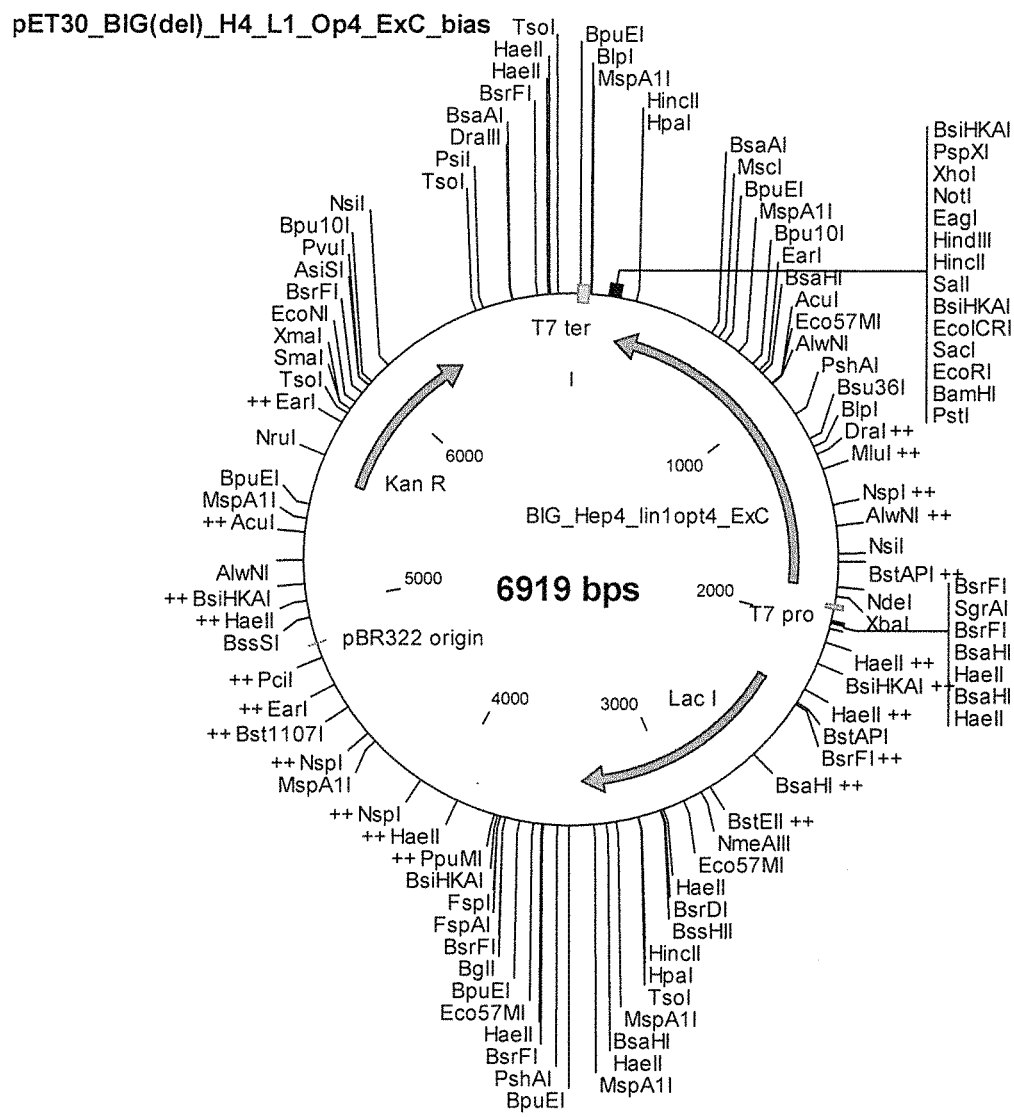
FIG. 15 is a restriction map of the 6919 bp vector for expression and secretion of the engineered Protein A construct BIG_Hep4_lin1opt4_ExC, cloned in a background of pET30B+. The Protein A construct is expressed from the T7 promoter transcribed counterclockwise.
Figure 16:
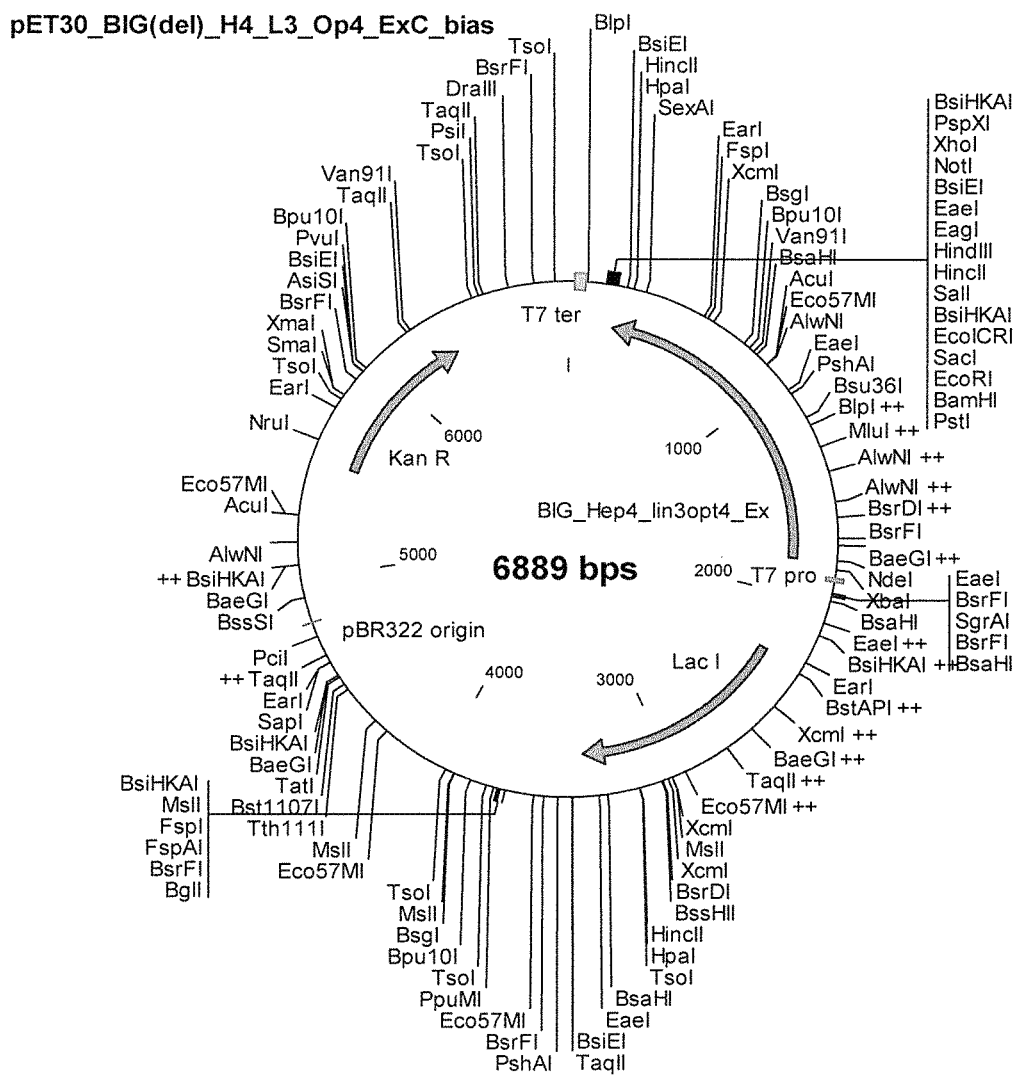
FIG. 16 is a restriction map of the 6889 bp vector for expression and secretion of the engineered Protein A construct BIG_Hep4_lin3opt4_ExC, cloned in a background of pET30B+. The Protein A construct is expressed from the T7 promoter transcribed counterclockwise.

The genes encoding the polypeptides having these amino acid sequences, SEQ ID NOs: 16 and 17, are shown in FIG. 14, were synthesized and ligated into the recipient plasmid, resulting in plasmids: BIG_Hep4_lin1opt4_ExC; and, BIG_Hep4_lin3opt4_ExC, see FIGS. 15 and 16, respectively. Plasmids were purified and restriction digestion with AvaI verified the expected size of restriction digestion fragments. Two single colony clones of each construct were chosen for analysis of expression and production optimization in cells of *E. coli* strain BL21λDE3 (commercially available from New England Biolabs).

Expression Optimization: Time, Temperature, Media, Additives.

Initial expression studies used shake flasks with TB complete medium, and growth of cells and production of polypeptide as analyzed as a function of time of culture. Control cells were the same strain carrying the empty vector without the polypeptide insert. Protein production of the engineered polypeptide was assessed by SDS-PAGE following induction of insert encoded protein by addition of IPTG to inactivate lac repressor and obtain the desired protein as a result of induction of synthesis of T7 polymerase, by methods well known to those of ordinary skill in recombinant plasmids and bacterial gene expression systems.

Production of the polypeptide was monitored in samples removed from each of the cultures at 3 h intervals. The polypeptides which are the engineered Protein A derivatives were observed to have appeared in culture supernatants beginning at 3 h after inoculation, and continuing to increase through 18 h of culture. No protein band having the same molecular weight was observed in the supernatants during growth for the same time periods of the control strain.

Figure 17:
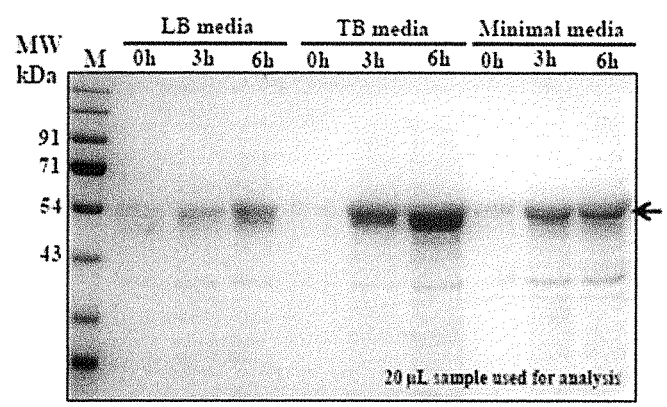
FIG. 17 is a photograph of an SDS-PAGE analysis of 20 µL samples of supernatants of cells carrying a gene encoding engineered Protein A construct BIG_Hep4_lin1opt4_ExC, cloned in a background of plasmid pET30B+, cultured in each of three media (LB, TB and M9 minimal medium), the samples taken at times indicated after induction of expression (each of 0 h, 3 h and 6 h). The arrow indicates the protein expressed having the predicted molecular weight. Molecular weight standards (MW kDa) were applied to the left hand lane.

Representative protein expression analytical data are shown in FIG. 17, which is a comparison of growth and production parameters for these strains in three standard *E. coli* media: LB (Luria-Bertani broth), TB (commercially available from Sigma), and M9 minimal media. Greatest polypeptide production was observed in TB, and the yield was estimated after 6 h of culture by SDS-PAGE to be at a level of at least about 250 mg/L. The minimal medium by comparison yielded about 180 mg/L. The SDS-PAGE data indicated that these supernatants contained predominantly the engineered polypeptide of interest, and small amounts of additional bands were see at lower molecular weights.

Expression was further compared at two temperatures of culture, and the result of that example was that production was observed to have been greater at 37° C. than at 30° C. Effects of potential medium additives were analyzed for the agents Glycine, Triton X-100 and Tween-20 which were added to TB medium and were present during growth. Analysis of culture supernatants by SDS-PAGE showed that each of these additives increased appearance of non-specific proteins in the supernatants, in comparison to control cultures in TB medium with no additives. The non-specific proteins were observed to be of higher and also lower molecular weights than the molecular weight of the engineered polypeptide.

Batch Fermentation and High-Cell Density Fed-Batch Fermentation.

Cells in TB medium were induced for production at high densities ($OD_{600}$ between 6 and 8) or very high density ($OD_{600}$ 40-50) and fermentation was monitored for $pO_2$, pH, temperature and growth profile. Samples were taken for determination of protein expression by SDS-PAGE analysis at time intervals after induction. Expression at high levels was observed in the supernatant in an almost pure form at a level equal to or greater than about 275 mg/L from batch fermentations, and at a level of about 1.2 g/L in the fed-batch fermentation.

Binding Capacity of Designed Polypeptides.

Surface plasmon resonance is used to analyze binding to each of eight sub-classes of human serum immunoglobulins by each of the Protein A polypeptides herein. Applicants envision that the polypeptides of SEQ NOs: 16 and 17 specifically bind IgG proteins to a greater extent per weight or per molecular weight of polypeptide, than parent Protein A as a control. Further, it is envisioned that arrays of affixed polypeptides display more resistance to washing and rinsing agents than control Protein A.

The invention claimed is:

1. A composition comprising an oligopeptide having amino acid sequence selected from the group consisting of: QPQMSHM (SEQ ID NO: 9); CPSTHWK (SEQ ID NO: 18); NVQYFAV (SEQ ID NO: 19); ASHTQKS (SEQ ID NO: 20); TNIESLK (SEQ ID NO: 21); NCHKCWN (SEQ ID NO: 22); and SHLSKNF (SEQ ID NO: 19), and further comprising an amino acid sequence of at least one functional moiety of at least one naturally occurring or recombinant immunoglobulin binding protein, the functional moieties being chosen for binding the Fc region of targeted classes of IgG immunoglobulins or immunoglobulin-containing compounds, the oligopeptide further being coupled to a separation matrix medium in a capture bed and characterized by flow rate kinetics.

2. The composition of claim 1, wherein the classes of IgG immunoglobulins or immunoglobulin-containing compounds are selected from the group consisting of IgG1, IgG2, IgG3, IgG4, IgM, IgA, IgE, and IgD.

3. The composition of claim 1, wherein a linking element connecting the oligopeptide and the amino acid sequence of the at least one functional moiety, the linking element having an amino acid sequence and containing fewer than about 1800 amino acids.

4. The composition of claim 3, wherein the linking element comprises fewer than about 95 amino acids.

5. The composition of claim 3, wherein the linking element comprises from about 2 to about 54 amino acids.

6. The composition of claim 3, wherein the linking element comprises from about 4 to about 10 amino acids.

7. The composition of claim 1, wherein the immunoglobulin binding protein has an amino acid sequence selected from the group consisting of: SEQ ID NOs: 1, 2, 3, 4, 5, 6, 7, 11, and 14 and portions thereof.

8. The composition of claim 1, wherein the separation matrix medium comprises a solid support comprising a medical-grade porous polyvinyl chloride (PVC) medium having a form selected from the group consisting of beads and sheets.

9. The composition of claim 8, wherein the solid support of the medical-grade PVC medium is embedded within or constitutes porous protein-adsorptive support surfaces, the medium having a bi-modal pore size distribution with the larger pore size ranging in average from about 0.5-5.0 micrometers and the smaller pore size ranging in average from about 0.003-0.3 micrometers.

10. The composition of claim 9, wherein the solid support and the support surfaces are coupled by singe-point attachment.

11. The composition of claim 9, wherein the solid support and the support surfaces are coupled by multi-point attachment.

12. The composition of claim 1, wherein the composition has an immunoglobulin binding capacity of the oligopeptide in mg per ml of bed volume is at least about 25.

* * * * *